US006364526B2

(12) United States Patent
Ivan et al.

(10) Patent No.: US 6,364,526 B2
(45) Date of Patent: *Apr. 2, 2002

(54) FLUORO-ASSIST FEATURE FOR A DIAGNOSTIC IMAGING DEVICE

(75) Inventors: Andrew J. Ivan, Reminderville; Leonard F. Plut, Mentor; Joseph S. Deucher, Lyndhurst; Pieter Gerhard Roos, Bainbridge; Kenneth L. Freeman, Stow; Marc Piscitelli, Richmond Heights; Dennis K. Everett, Seven Hills, all of OH (US)

(73) Assignee: Philips Medical Systems (Cleveland) Inc., Highland Heights, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/480,514

(22) Filed: Jan. 10, 2000

Related U.S. Application Data

(62) Division of application No. 08/979,571, filed on Nov. 26, 1997, now Pat. No. 6,031,888.

(51) Int. Cl.[7] .................................................. H05G 1/64
(52) U.S. Cl. ...................................... 378/198; 378/98.8
(58) Field of Search ................................ 378/198, 98.8

(56) References Cited

U.S. PATENT DOCUMENTS

| | | |
|---|---|---|
| 2,818,510 A | 12/1957 | Verse |
| 4,150,297 A | 4/1979 | Borggren |
| 5,327,474 A | 7/1994 | Inoue et al. |

(List continued on next page.)

FOREIGN PATENT DOCUMENTS

| | | |
|---|---|---|
| JP | 56155937 | 12/1981 |
| JP | 08052131 | 2/1996 |
| JP | 09045952 | 2/1997 |

OTHER PUBLICATIONS

"Percutaneous Vertebroplasty Guided By a Combination of CT and Fluoroscopy" Afshin Gangi, et al., *AJNR* 15:83–86, Jan. 1994.

"The Interventional CT and Fluoroscopy Room" Z.L. Barbaric, MD, et al. *Abstract, Radiology*, Nov., 1996, vol. 201P p. 475.

Large Area, Flat–Panel a–Si:H Arrays for X–Ray Imaging, L.E. Antonuk, et al. SPIE vol. 1896 *Physics of Medical Imaging* (1993).

(List continued on next page.)

*Primary Examiner*—Craig E. Church
(74) *Attorney, Agent, or Firm*—Fay, Sharpe, Fagan, Minnich & McKee, LLP

(57) ABSTRACT

A frame (A) of a diagnostic imaging device such as a CT scanner or an MRI device has a bore defining a patient examination region (12). A first x-ray source (B) is mounted to a frame (C) for rotation around the examination region (12). An arc of first radiation detectors (14) detects x-rays which have traversed the examination region. A first image reconstruction processor (18) reconstructs a tomographic image representation from signals generated by the first radiation detectors. A fluoroscopy device (D) is mechanically coupled to the diagnostic scanner for generating and displaying at least substantially real-time fluoroscopic projection image representations on a display monitor (60). A second x-ray source (32) transmits x-rays to an amorphous silicon flat panel radiation detector (36). A second image reconstruction processor (58) reconstructs the fluoroscopic projection image representations from signals generated by the flat panel radiation detector (36). A C-arm (30) supports the second x-ray source (32) and the flat panel radiation detector (36) in a plane offset from a plane of the C-arm. A movable mounting structure (E) is mechanically connected with the gantry (A) and the C-arm (30) to move the C-arm between a stored position and an operating position adjacent the bore.

20 Claims, 21 Drawing Sheets

U.S. PATENT DOCUMENTS

| | | | |
|---|---|---|---|
| 5,448,610 A | | 9/1995 | Yamamoto et al. ............ 378/19 |
| 5,525,905 A | | 6/1996 | Mohapatra et al. |
| 5,583,909 A | * | 12/1996 | Hanover ...................... 378/198 |
| 5,592,523 A | | 1/1997 | Tuy et al. |
| 5,661,772 A | | 8/1997 | Bär et al. ...................... 378/20 |
| 5,877,501 A | * | 3/1999 | Ivan et al. .................. 378/98.8 |
| 5,949,846 A | * | 9/1999 | Stein et al. .................... 378/54 |
| 5,949,848 A | * | 9/1999 | Gilblom .................... 378/98.8 |

OTHER PUBLICATIONS

Development of Hydrogenated Amorphous Silicon Sensors for High Energy Photon Radiotherapy Imaging, L.E. Antonuk, et al. *IEEE Transactions on Nuclear Science,* vol. 37, No. 2, Apr. 1990.

Radiation Imaging with 2D a–Si Sensor Arrays, I. Fujieda, et al. *IEEE Transactions on Nuclear Science,* vol. 39, No. 4, 1992.

Development of Hydrogenated Amorphous Silicon Sensors for Diagnostic X–Ray Imaging, L.E. Antonuk, et al. *IEEE Transactions on Nuclear Science,* vol. 38, No. 2, Apr., 1991.

A High Resolution, High Frame Rate, Flat–Panel TFT Array for Digital X–Ray Imaging, L.E. Antonuk, et al., SPIE vol. 2163 *Physics of Medical Imagaing* (1994).

Digital Radiology Using Self–Scanned Readout of Amorphous Selenium, W. Zhao, et al., SPIE vol. 1896 *Physics of Medical Imaging* (1993).

Amorphous Silicon X–Ray Imaging Sensor, J. Chabbal, et al. SPIE's Symposium "Medical Imaging 1996", 10–15 FCS, Newport Beach.

SWISSRAY Advertisement, *Medical Imaging,* vol. 12, No. 9, Sep., 1997.

FischerImaging Product Data Sheet—Ceiling Suspended Imaging System.

* cited by examiner

FLUORO-ASSIST FEATURE FOR A DIAGNOSTIC IMAGING DEVICE

This appln. is a Div of Ser. No. 08/979,571, filed Nov. 26, 1997, now U.S. Pat. No. 6,031,888.

BACKGROUND OF THE INVENTION

The present invention relates to the medical diagnostic imaging arts. It finds particular application in conjunction with a diagnostic imaging device such as a computerized tomographic (CT) scanner and a Magetic Resonace Imaging (MRI) apparatus, which includes a fluoro-assist device, and will be described with particular reference thereto. However, it should be appreciated that the present invention may also find application in conjunction with other multi-modality medical imaging systems such as nuclear medicine scanners, etc. where a fluoro-assist device may be useful.

When performing minimally invasive or certain interventional procedures such as abscess drainages, CT arterial portography, TIPS, and catheter placement for organ assessment, catheters are typically placed or positioned in a patient in a fluoroscopy room or suite. The patient, with the catheter in place, is then moved to a CT suite where the procedure is then performed.

A number of disadvantages exist when moving a patient between a fluoroscopy suite and a CT suite. For instance, the danger exists that the catheter may move or shift within the patient during transport from the fluoroscopy suite to the CT suite. Further, the scheduling and availability of both suites can be complicated. In other cases, when a lesion is diagnosed during a CT procedure, the patient must then be rescheduled for a needle biopsy, or the biopsy is performed with the CT scanner alone, which is complicated and takes a long time to perform.

It is known to use a mobile C-arm fluoroscopy device to provide fluoro images during interventional procedures performed in a CT suite. However, mobile C-arm fluoroscopy devices are not always available when needed. In addition, known C-arm fluoroscopy devices, including mobile C-arm fluoroscopy devices, use large, cylindrical image intensifier tubes which are difficult to maneuver and position adjacent a CT gantry.

Further, the interventionalist must stand beside the image intensifier tube to access the patient during an interventional procedure, which may be an awkward position for the interventionalist and which also increases the radiation dose to the interventionalist. It is also known that image intensifier tubes tend to introduce image distortion due to the glass curvature and magnetic effects. Present mobile C-arms are big and bulky, and because of their size, they are difficult to store, and are typically in the way when not in use.

It is known to use a CT system to provide a fluoro image for interventional work. However, using the CT system for fluoro imaging requires a physician to work on the patient in the bore of the CT gantry which is awkward for the physician, and which generates a significantly higher radiation dose to both the patient and the surgeon. Further, the CT system can only produce fluoro images which are in the same plane as the CT system.

It is also known to rotate, pivot, or swing a common patient support between a CT scanner and an angiographic (i.e., fluoroscopic) unit. However, the patient is still moved when the patient support is rotated between the two pieces of diagnostic equipment. In addition, linking a separate CT scanner with an angiographic unit via a common, rotatable, patient support is an expensive alternate solution.

Accordingly, it has been considered desirable to develop a new and improved fluoro assist feature for an imaging system which meets the above-stated needs and overcomes the foregoing difficulties and others while providing better and more advantageous results.

SUMMARY OF THE INVENTION

In accordance with one aspect of the present invention, a diagnostic imaging apparatus is disclosed. The diagnostic imaging apparatus includes a frame defining an examination region. A diagnostic imaging subsystem generates first diagnostic image representations of an object when the object is positioned within the examination region. A patient support is adapted for movement through the examination region. A fluoroscopic imaging subsystem generates fluoroscopic image representations of the object. The fluoroscopic imaging subsystem includes an x-ray source for transmitting x-rays, a flat panel image receptor for detecting the x-rays and generating signals indicative of the detected x-rays, and a support member for supporting the flat panel image receptor in a stored position remote from the patient support and an operating position proximate the patient support.

In accordance with another aspect of the present invention, a diagnostic imaging apparatus is disclosed. The diagnostic imaging apparatus includes a frame defining an examination region, a diagnostic imaging subsystem for generating a first diagnostic image representation of an object when the object is positioned within the examination region, and a patient support adapted for movement through the examination region. A fluoroscopic imaging subsystem is mechanically coupled to the frame, and includes a flat panel image receptor which detects x-rays and generates signals indicative of the detected x-rays.

In accordance with yet another aspect of the present invention, a method of generating fluoroscopic projection image representations with a diagnostic imaging apparatus, is disclosed. The diagnostic imaging apparatus includes a frame defining an examination region, a first diagnostic imaging subsystem for generating diagnostic image representations of an object when the object is positioned within the examination region, and a patient support adapted for movement through the examination region. The method includes moving a flat panel image detector that is mechanically coupled to the frame from a stored position remote from the patient support to an operating position proximate the patient support, the radiation detector panel detecting x-rays generated by an x-ray source and generating signals indicative of the radiation detected, and reconstructing the fluoroscopic projection image representations from the signals generated by the radiation detector panel.

In accordance with a further aspect of the present invention, a fluoroscopy imaging device which generates at least one of a fluoroscopic image representation and a radiographic image representation of an object is disclosed. The fluoroscopy imaging device includes a mobile cart, an x-ray source for transmitting x-rays, a flat panel image receptor for detecting the x-rays and generating signals indicative of the detected x-rays, and a support member secured to the mobile cart for supporting the x-ray source and the flat panel image receptor.

One advantage of the present invention is the provision of a fluoro-assist device for a CT scanner which is readily available when needed.

Another advantage of the present invention is the provision of a fluoro-assist device for a CT scanner which permits real-time imaging of minimally invasive tools (catheters, needles, etc.) that are inserted in a CT suite.

Yet another advantage of the present invention is the provision of a fluoro-assist device for a CT scanner where a interventionalist can work behind a flat panel image receptor which acts as a primary barrier to radiation exposure.

Still another advantage of the present invention is the provision of a fluoro-assist device for a CT scanner which incorporates a flat panel image detector.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

Figure 1:
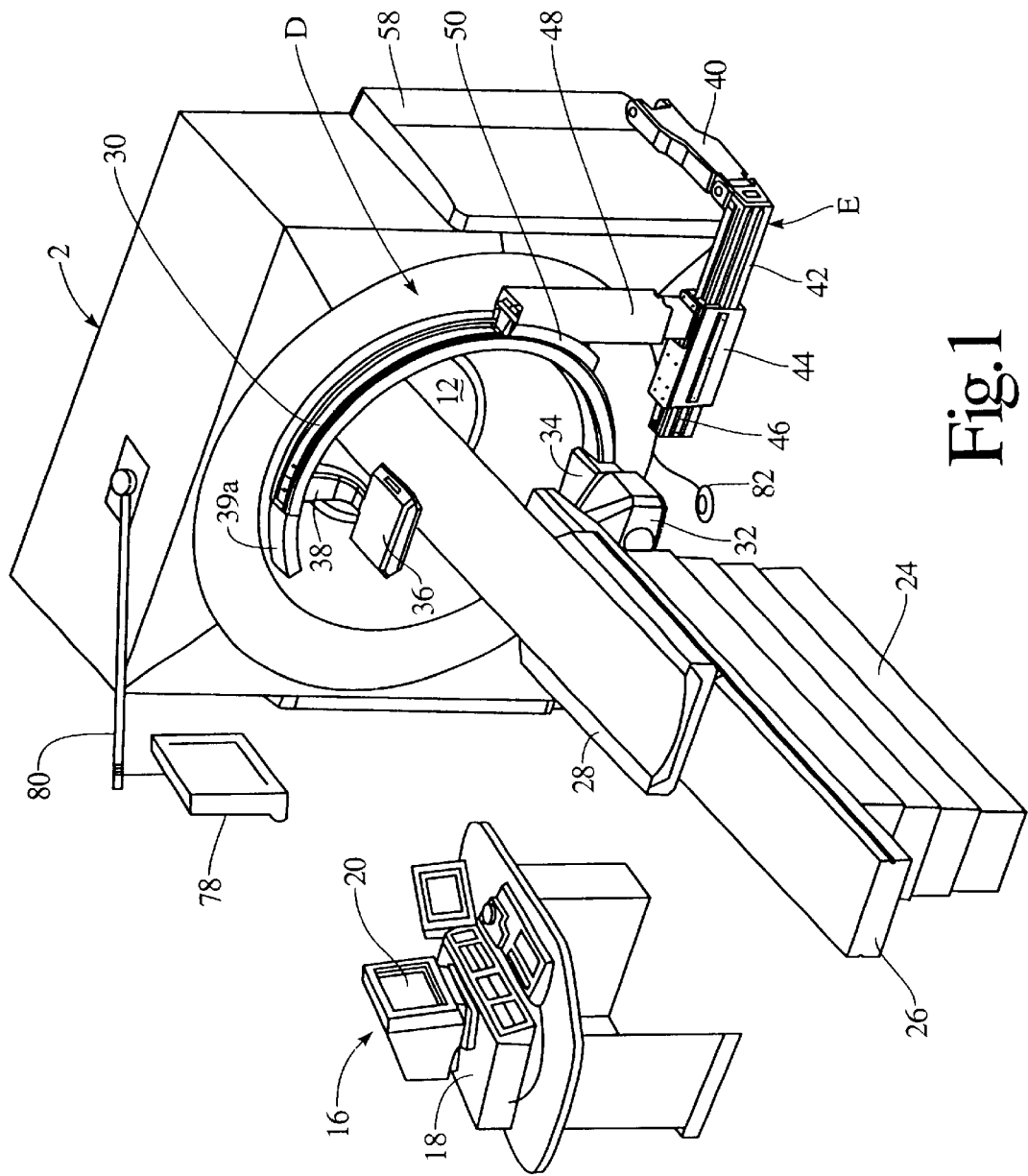
FIG. 1 is a perspective view of an exemplary diagnostic imaging device such as a CT scanner or a Magnetic Resonance Imaging (MRI) apparatus having an integrated fluoro-assist device with a C-arm shown in an operating position.
Figure 2:
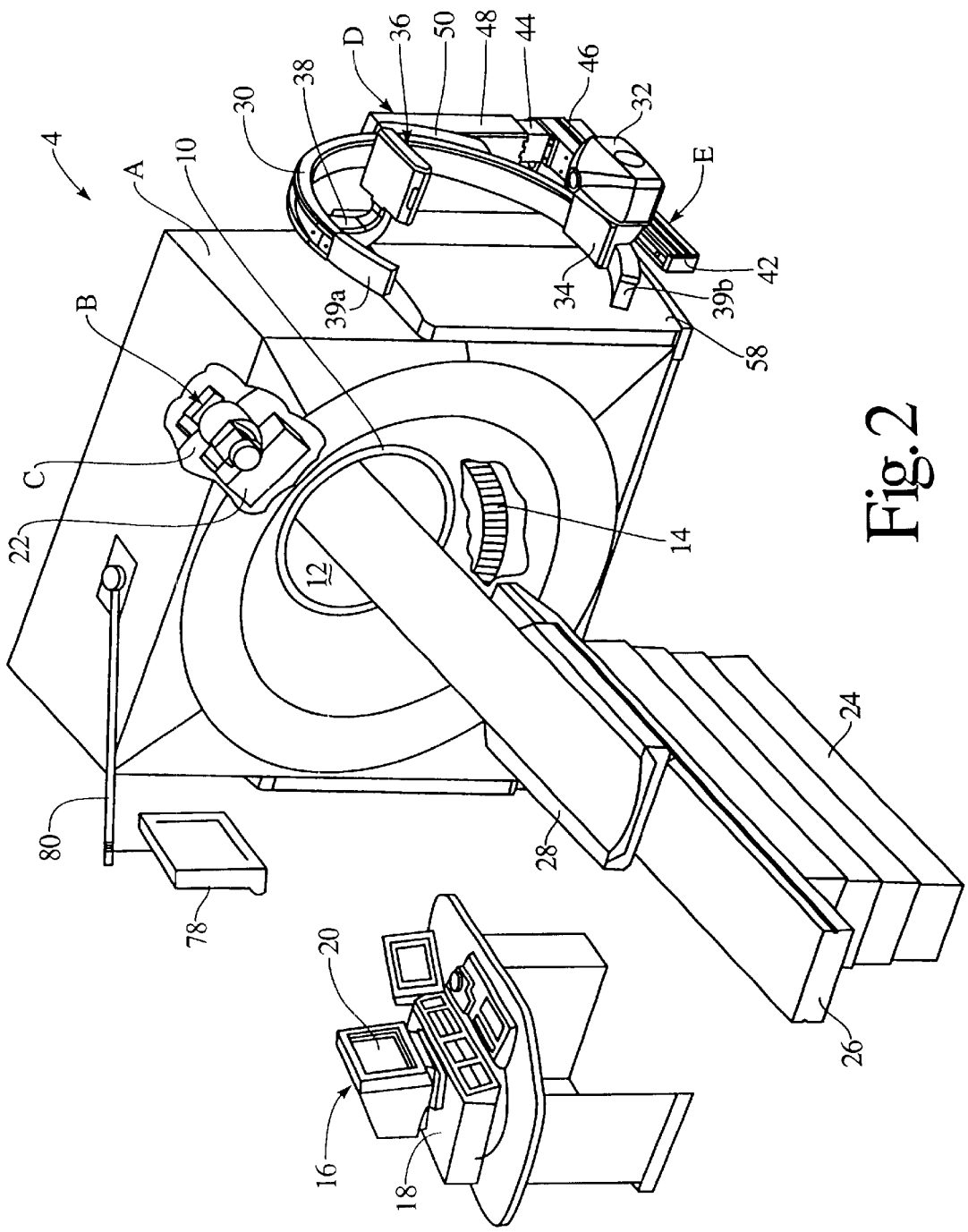
FIG. 2 is a perspective view of the CT scanner of FIG. 1 with the C-arm shown in a stored position adjacent the CT gantry.

With reference to FIGS. 1 and 2, an exemplary diagnostic imaging system 2, such as a CT scanner 4, includes a floor-mounted, non-rotating frame member or gantry A whose position remains fixed during data collection. An x-ray tube B is rotatably mounted on a rotating frame member or gantry C. The stationary gantry A includes a cylinder 10 that defines a patient examination region 12. An array of radiation detectors 14 are disposed concentrically around the patient receiving region. In the illustrated embodiment, the x-ray detectors are mounted on the stationary gantry portion such that an arc segment of the detectors receives radiation from the x-ray tube B which has traversed the examination region 12. Alternatively, an arc segment of radiation detectors can be mounted to the rotating gantry to rotate with the x-ray tube. The x-ray tube B and radiation detectors 14 comprise a diagnostic imaging subsystem of the diagnostic scanner.

A control console 16 contains an image reconstruction processor 18 for reconstructing an image representation out of signals from the detector array 14. Preferably, the image reconstruction processor reconstructs a volumetric image representation from radiation attenuation data taken along a spiral path through the patient. A video monitor 20 converts selectable portions of the reconstructed volumetric image representation into a two-dimensional human-readable display. The console 16 includes tape and disk recording devices for archiving image representations, and also includes circuitry for performing image enhancements, selecting planes, 3D renderings, or color enhancements, and the like. Various scanner control functions such as initiating a scan, selecting among different types of scans, calibrating the system, and the like, are also performed at the control console 16.

The x-ray tube B includes an oil filled housing that has an x-ray permeable window directed toward the patient receiving region. An evacuated envelope is disposed within the housing and contains a rotating anode, such as a 7-inch anode, and a cathode or other electron source. High voltages, on the order of 150 kV applied between the rotating anode and the cathode, cause the generation of x-rays. The x-rays pass through the x-ray permeable window and across the patient receiving region 12.

Appropriate x-ray collimators 22 focus the radiation into one or more planar beams which span the examination region 12, as is conventional in the art. The console 16 includes circuitry for gating the x-ray source B to control patient dosage. A high voltage power supply is mounted on the rotating gantry for rotation with the x-ray tube.

A fixed patient table 24 is positioned adjacent the diagnostic scanner so as to extend from the examination region 12 in a first direction substantially along a central axis of the cylinder 10. A patient beam 26 is secured to an upper surface of the patient table 24. A patient couch 28 is slidably secured to the patient beam 26 for back and forth movement through the examination region 12 along the beam 26. It should be appreciated that at least the patient couch can be configured to pan laterally relative to a longitudinal axis of the gantry bore. The table 24, beam 26, and couch 28, cooperate to define a patient support which is adapted for movement through the examination region.

An integrated fluoroscopy or fluoro-assist device D is secured to the gantry A for movement between an operating position (FIG. 1) and a stored position (FIG. 2). The fluoro-assist device includes a support member that is movably secured to either side of the gantry A via a mounting structure E. In the embodiment being described, the support member is a C-arm 30.

A fluoroscopic x-ray source or tube 32 is secured proximate a first end of the C-arm 30 via a cantilevered support bracket 34. Likewise, an opposing x-ray detector 36 is secured proximate a second end of the C-arm 30 via a cantilevered support bracket 38. An upper counterweight 39a extends from the first end of the C-arm and a lower counterweight 39b extends from the second end of the C-arm. The x-ray source 32 and detector 36 cooperate to define a fluoroscopic imaging subsystem of the diagnostic scanner.

In the embodiment being described, the mounting structure E includes a first link or support arm 40 having one end pivotally secured to the gantry A and the other end pivotally secured to a second link or support arm 42. A first upright support arm 44 is movably secured to the second arm 42 for substantial horizontal movement along a track 46 associated with the second arm 42. A second upright support arm 48 is movably secured to the first upright support arm 44 for substantial vertical movement along a common longitudinal axis of the upright support arms 44, 48. The C-arm 30 is rotatably supported by a bearing assembly 50 associated with the second upright support arm 48 which permits the x-ray source 32 and detector 36 to rotate about a geometric center of the C-arm through an arc of at least 180°.

The mounting structure E permits the C-arm to be conveniently stored or parked along the side of the gantry when not in use, and, when needed, to be positioned in front of the gantry with the x-ray source 32 placed directly under the patient table. In particular, the first support arm 40 pivots approximately 180° around the gantry when moving the C-arm between the stored position and the operating position. Further, the second support arm 42 pivots approximately 90° around the first support arm 40 when moving the C-arm between the stored position and the operating position. However, it should be appreciated that the C-arm can be mounted to any other part of the gantry.

The bearing assembly 50 permits the C-arm 30, and thus the x-ray source 32 and detector 36, to be rotated around a longitudinal axis of the patient from the "under table" position shown in FIG. 1, to a lateral position on either side of the patient table. This provides a ±90°, or any angle in-between, movement of the x-ray source 32 and detector 36 from the "under table" position to provide lateral imaging from both sides of the patient.

The C-arm 30 moves vertically as the second upright support arm 48 telescopically extends and retracts vis-à-vis the first upright support arm 44 to permit easier access to the patient and to adjust image magnification. The C-arm also moves laterally across the patient with the first and second upright support arms 44, 48 vis-à-vis the track 46 to allow lateral image panning across a patient's body. Longitudinal image panning (i.e. along a patient's body) is accomplished by automatically or manually driving the patient couch 28 in either or both directions along the rail 26. It should be appreciated that the bearing assembly 50 could permit the plane of the C-arm to rotate or tilt from an orientation normal to an axis of the patient support (e.g. to a position with the x-ray source 32 over the patient table and the detector 36 under the patient table). Thus, an operating position of the flat panel image detector is broadly defined herein as any position or orientation (i.e. above, below, adjacent, etc.) of the detector 36 relative to the patient support without regard to the position of the detector relative to the gantry bore (i.e., within the bore or proximate the bore). The stored position of the detector 36 is defined as a position which is remote from at least one of the patient support and the gantry bore.

Figure 3:
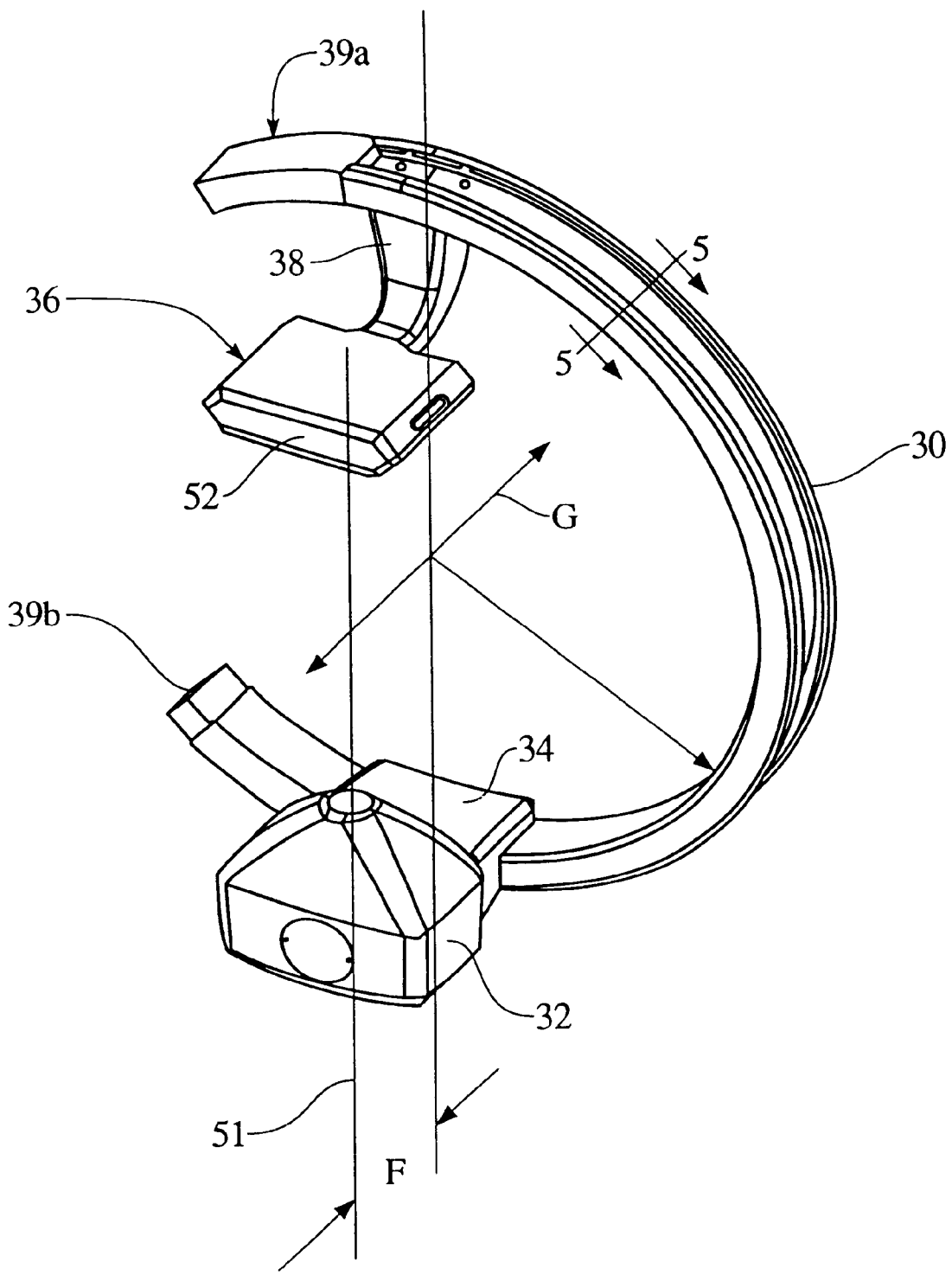
FIG. 3 is a perspective view of the C-arm of FIGS. 1 and 2.

Referring now to FIG. 3, the x-ray source 32 and the detector 36, and more particularly a centerline 51 of the imaging system, is offset a distance F from a plane of the C-arm by the cantilevered support brackets 34, 38. A fluoroscopic examination region is defined between the x-ray source and detector substantially along the centerline 51. By offsetting the x-ray source and detector offset from the C-arm, interference caused by the C-arm during interventional procedures is minimized.

The centerline 51 of the imaging system intersects with the orbit axis G of the C-arm. As a result, both the geometric center of the C-arm 30 and the imaging system centerline 51 are positioned at iso-center during a fluoroscopic imaging procedure. The imaging system centerline 51 rotates around, but does not shift laterally relative to, iso-center when the C-arm is orbited.

In contrast, with known C-arm systems, the centerline of the imaging system is laterally offset from the orbit axis of the C-arm. During an imaging procedure, the centerline of the imaging system is positioned at iso-center and the orbit axis of the known C-arm is laterally offset from iso-center. When the known C-arm is rotated about its orbit axis, the imaging system centerline shifts off iso-center. Thus, in order to maintain the imaging system centerline at iso-center when a known C-arm system is orbited, the whole C-arm must be laterally repositioned in addition to being orbited.

Figure 4:
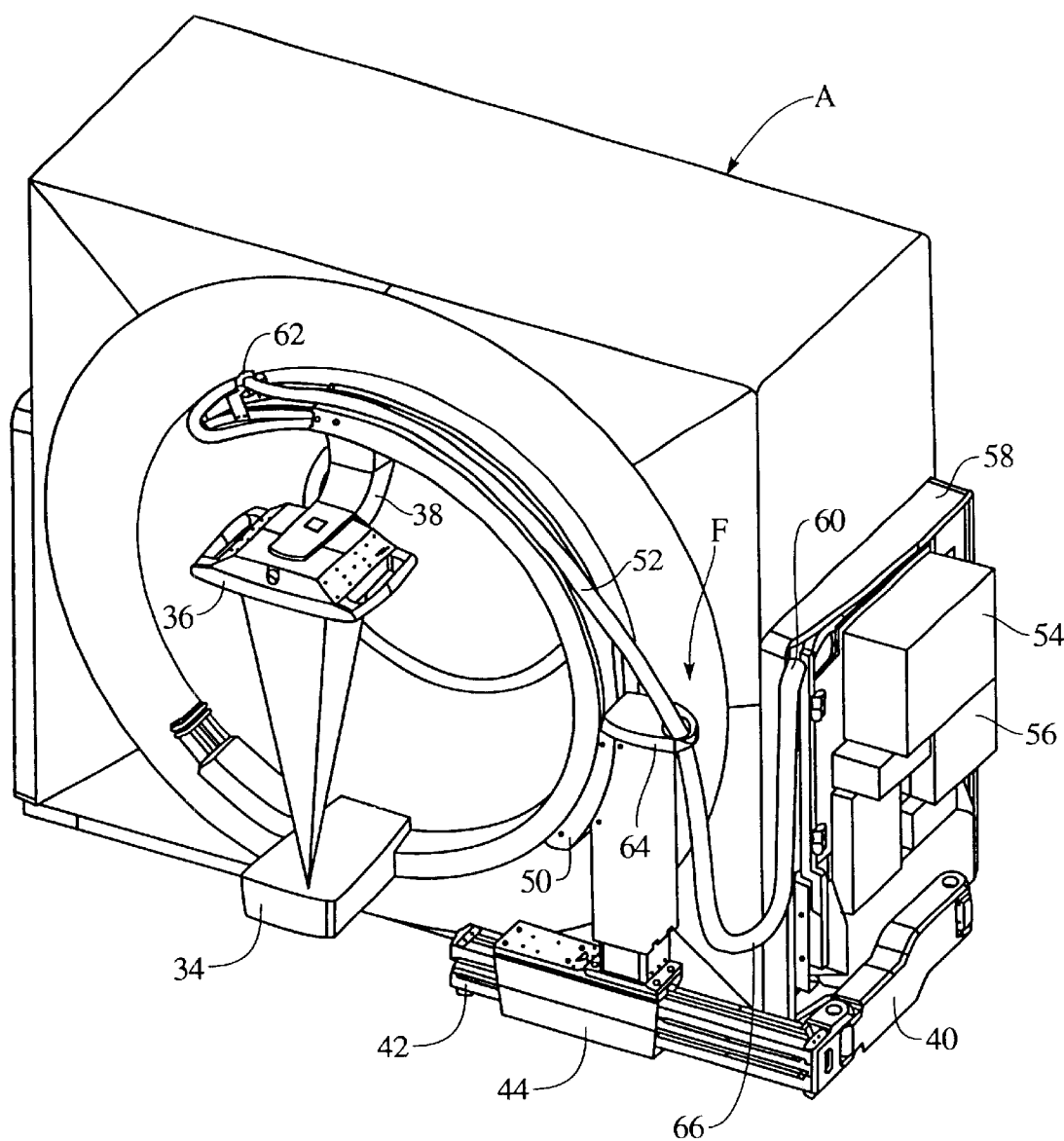
FIG. 4 is a perspective of the CT scanner of FIG. 1 showing a C-arm take-up/tension control system.
Figure 5:
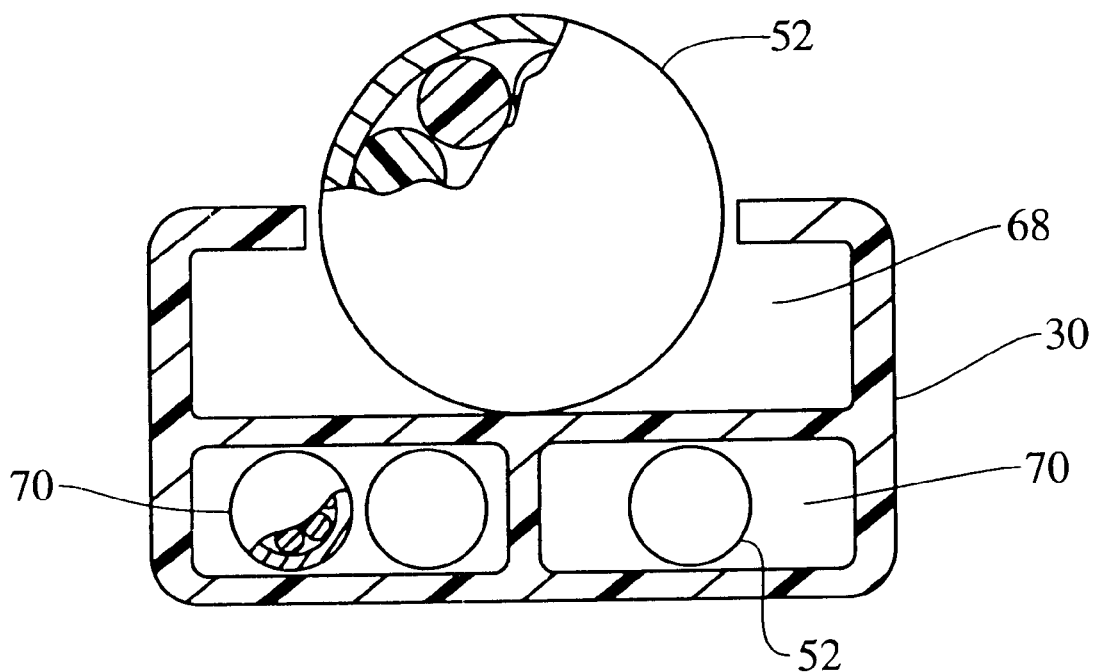
FIG. 5 is a cross section view of the C-arm taken along the line 5—5 of FIG. 3.

Referring now to FIGS. 4 and 5, a cable take-up/tension control system F for the C-arm 30 is shown. It should be appreciated that the C-arm is shown with one or more protective covers removed. One or more data/power cables 52 connect the x-ray source 32 and detector 36 to a fluoro-image reconstruction computer 54 and power supply 56 housed in a cabinet 58 which is mounted to the side of the gantry. A first hose anchor 60 secures an intermediate portion of the cable 52 to the cabinet 58. A second hose anchor 62 secures another intermediate portion of the cable to the upper end of the C-arm. A cable guide 64 is positioned on or above the second upright support arm 48 proximate the bearing assembly 50. The cable guide includes an aperture through which the cable 52 slidably passes. The portion of the cable 52 extending between the cable guide 64 and the first anchor 60 forms a variable length service loop 66. A portion of the cable 52 extending between the cable guide 64 and the second anchor 62 rests at least partially within an open channel 68 defined within an exterior surface of the C-arm. When the C-arm is rotated in a clockwise direction from the upright position shown in FIG. 4, a portion of the cable 52 resting within the channel 68 passes through the cable guide 64 and is taken up by the service loop 66. Likewise, when the C-arm is rotated in a counter-clockwise direction, a portion of the cable 52 defining the service loop 66 passes through the cable guide 64 and is guided into the channel 68.

A portion of the cable 52 extending past the second anchor 62 wraps around the upper counterweight 39a and passes through one or more closed channels 70 forming an inner portion of the C-arm 30. A portion of the cable 52 within the C-arm channels 70 pass through the support arms 34, 38 to connect to the x-ray source 32 and detector 36, respectively.

Figure 6:
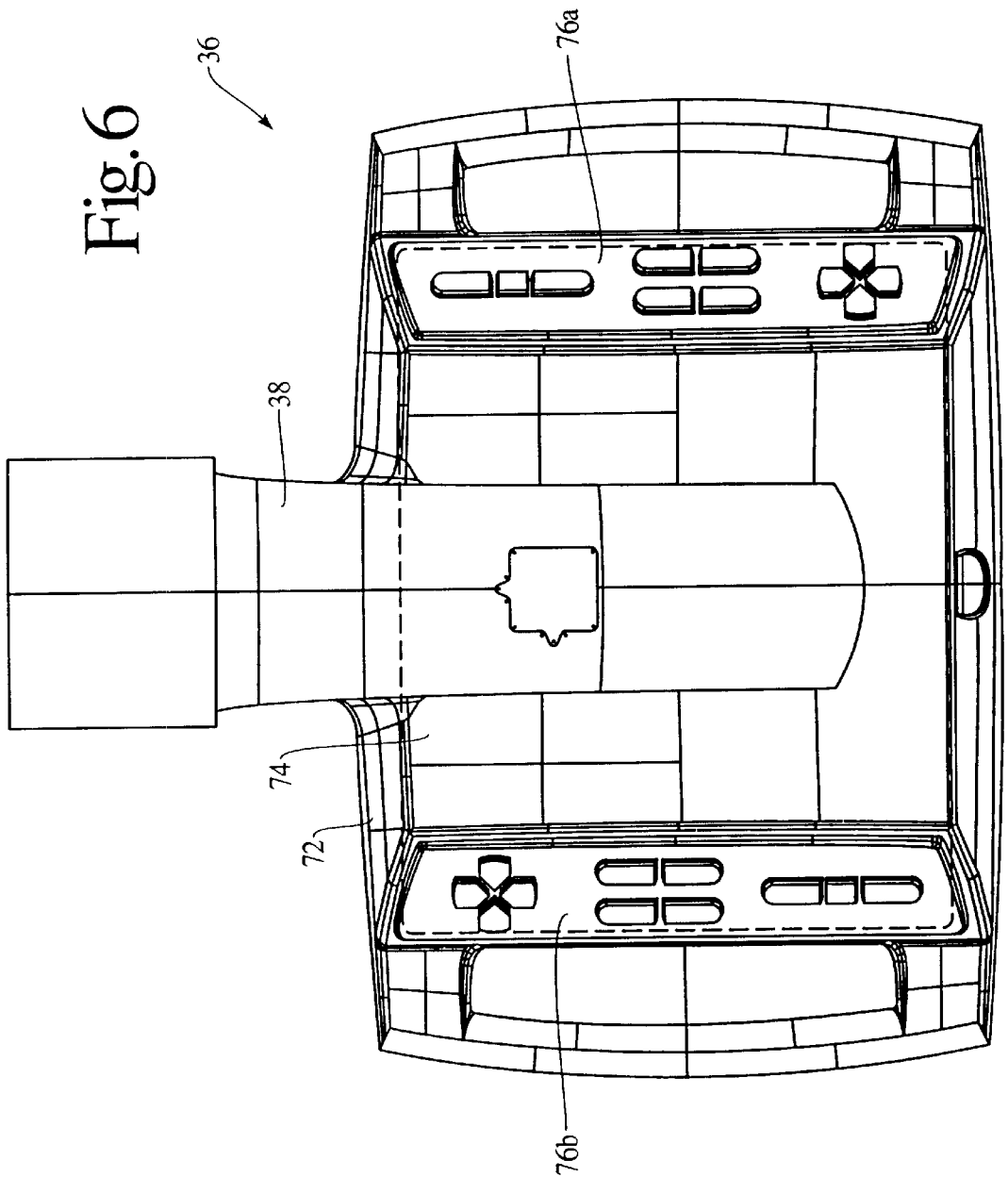
FIG. 6 is a top plan view of an image detector housing mounted to the C-arm.

Referring now to FIG. 6, the detector 36 includes a housing 72 which supports a flat panel image receptor or array 74 (shown in phantom) of individual image receptors. A "flat panel image receptor" as used herein includes a planar substrate such as glass laminated with an array of sensors such as amorphous silicon crystals that convert x-ray energy to electrical signals. That is, the sensors emit an electronic potential when struck by photons of x-ray energy. The intensity of the potential is related to the intensity of the x-ray beam. The electrical signals can be read out from a row/column matrix and then converted to digital data.

In the embodiment being described, an amorphous silicon flat panel image receptor includes a Cesium Iodide scintillating layer on an amorphous silicon glass substrate. The scintillating layer converts x-ray energy into light. An array of photodiodes on the glass substrate convert the light into electrical signals. The electrical signals are readout of a row/column matrix that is accessed using thin film transistor switches on the amorphous silicon substrate. The analog data is then converted to a digital format.

The amorphous silicon flat panel image receptor is compact in size and weight and replaces the conventional image intensifier tube, thus reducing the size of the detector 36. The mechanical support (i.e. support arm 38) for the detector 36 is also reduced in size and weight. Further, the flat panel image receptor 74 provides a rectangular image, eliminates the distortion of an image common to conventional image intensifier tubes, and provides constant image quality across the flat panel of the image receptor, thus minimizing the amount of panning typically required with conventional image intensifier tubes. It should be appreciated that the flat panel image receptor can be of any dimension such as 20 cm×25 cm, and the system can be easily upgraded to incorporate larger flat panel image receptors. It is contemplated that a fluoro-assist device having a conventional image intensifier or alternate technology can be mechanically coupled to an imaging system in the same or similar manner as described above.

The housing 72 includes two handles integrally formed therein. A first control panel 76a is mounted at one end of the housing 72 adjacent one handle, and a second control panel 76b is mounted on the opposite end of the housing adjacent the other handle. Depending upon the particular orientation of the C-arm, either control panel 76a, 76b can be used to adjust the position (i.e. rotate) the C-arm, depending upon which control panel is most accessible to the operator.

When the C-arm 30, and thus the x-ray source 32 and detector 36, is rotated to a lateral position on either side of the patient table, a physician performing an interventional procedure may position himself/herself behind the offset detector housing 72 to prevent direct exposure to the x-ray beam generated by the source 32, and to reduce exposure due to scattered radiation. The flat panel image receptor 74 may incorporate a lead shielding layer or other radiation absorbing material therein to minimize radiation exposure to the medical personnel. Alternatively, a lead shield may be incorporated into the housing 72.

As described above, the flat panel image receptor 74 within the housing 72 is coupled to the fluoro-image processing computer 54 housed in the cabinet 58 mounted to the side of the gantry. The fluoro-image processing computer 54 processes the acquired image from the detector 36 and permits an operator to adjust window and level functions of the displayed image. The fluoro-image generated by the fluoro-image reconstruction computer is displayed on an adjustable monitor 78 (FIGS. 1 and 2) connected to the gantry via a lateral support arm 80. Alternatively, the monitor 78 can be suspended from the ceiling, or located on a cart. The monitor 78 can be either a flat panel monitor or a standard CRT monitor. In addition, the fluoro-image output could go directly to a filming device. The fluoro-image output could also go to the diagnostic system and be displayed with the volumetric images on the display 20.

The fluoro-assist device D may be activated and deactivated with a foot pedal 82 (FIG. 1) in a conventional manner. When activated, the fluoro exposure can be either continuous or pulsed. In the pulsed mode, radiography procedures can be performed, such as CINE, Spot Film and DSA, thereby generating radiographic image representations. The x-ray source 32 can be gated on and off in the pulsed mode using a conventional grid control circuitry or a pulse fluoro high-voltage power supply.

Figure 7:
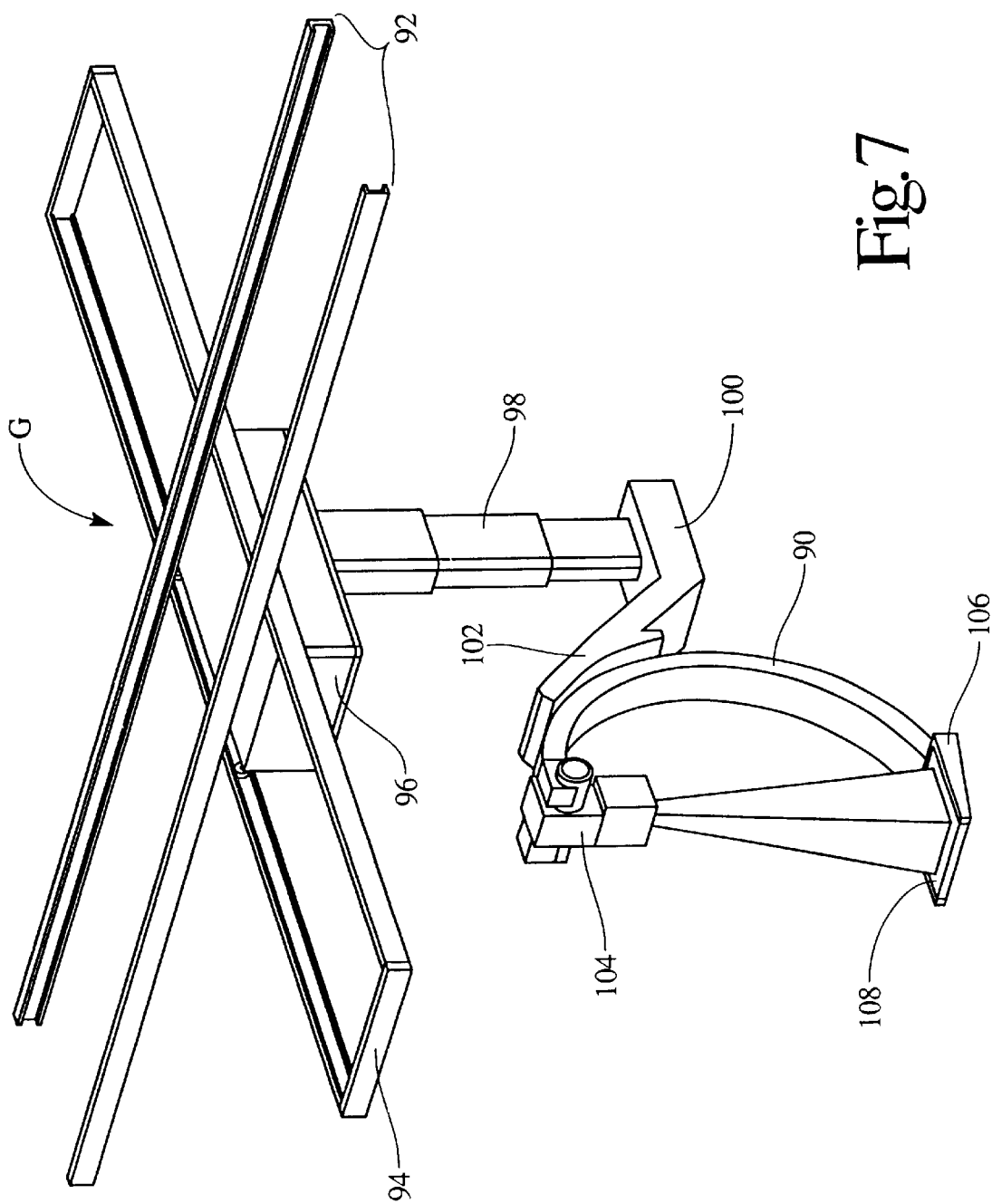
FIG. 7 is a perspective view of a second embodiment of an integrated fluoro-assist device having a C-arm mounted to an overhead track.
Figure 8:
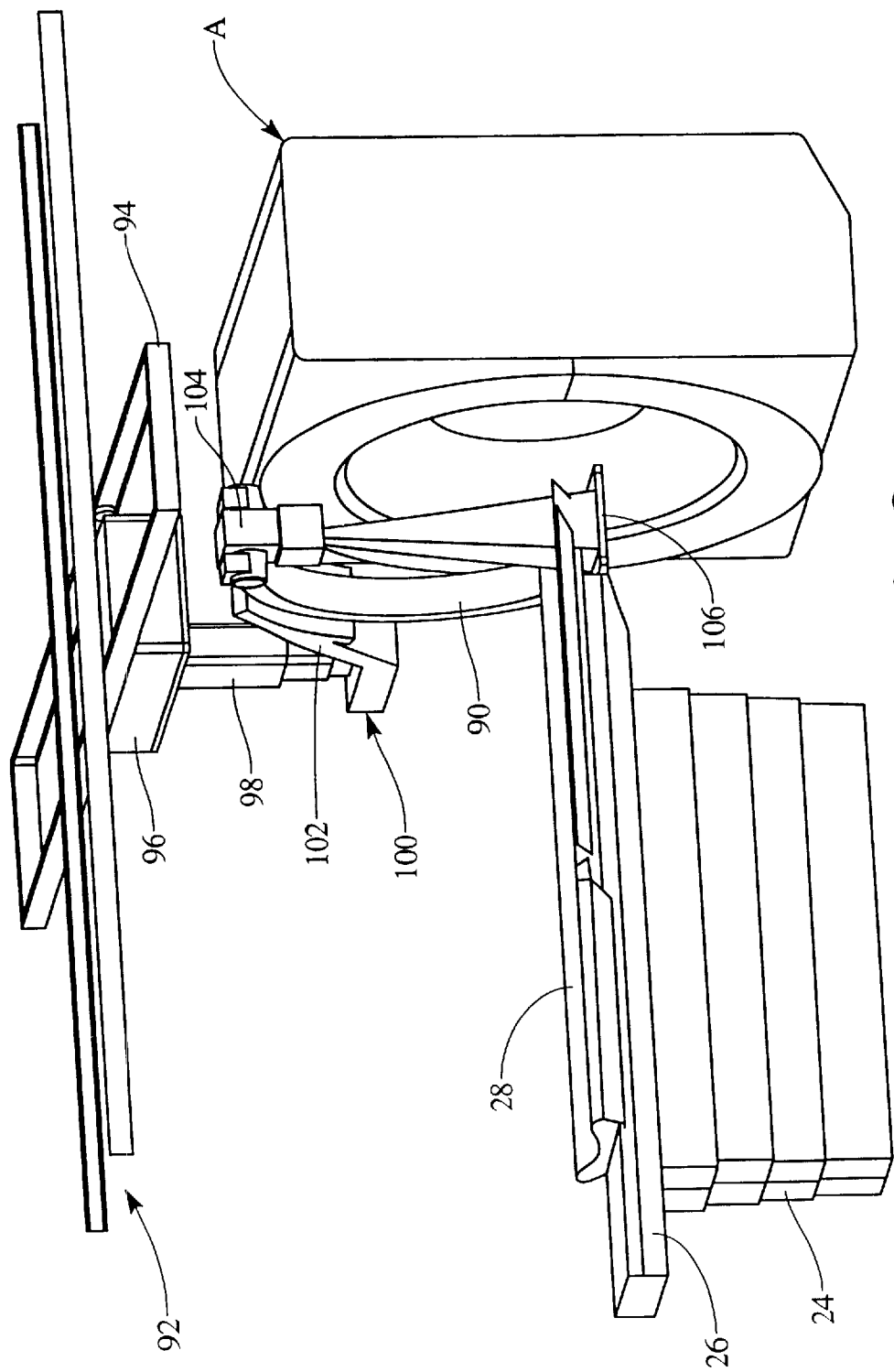
FIG. 8 is a perspective view of a CT scanner with the overhead C-arm of FIG. 7 positioned in front of the CT gantry.
Figure 9:
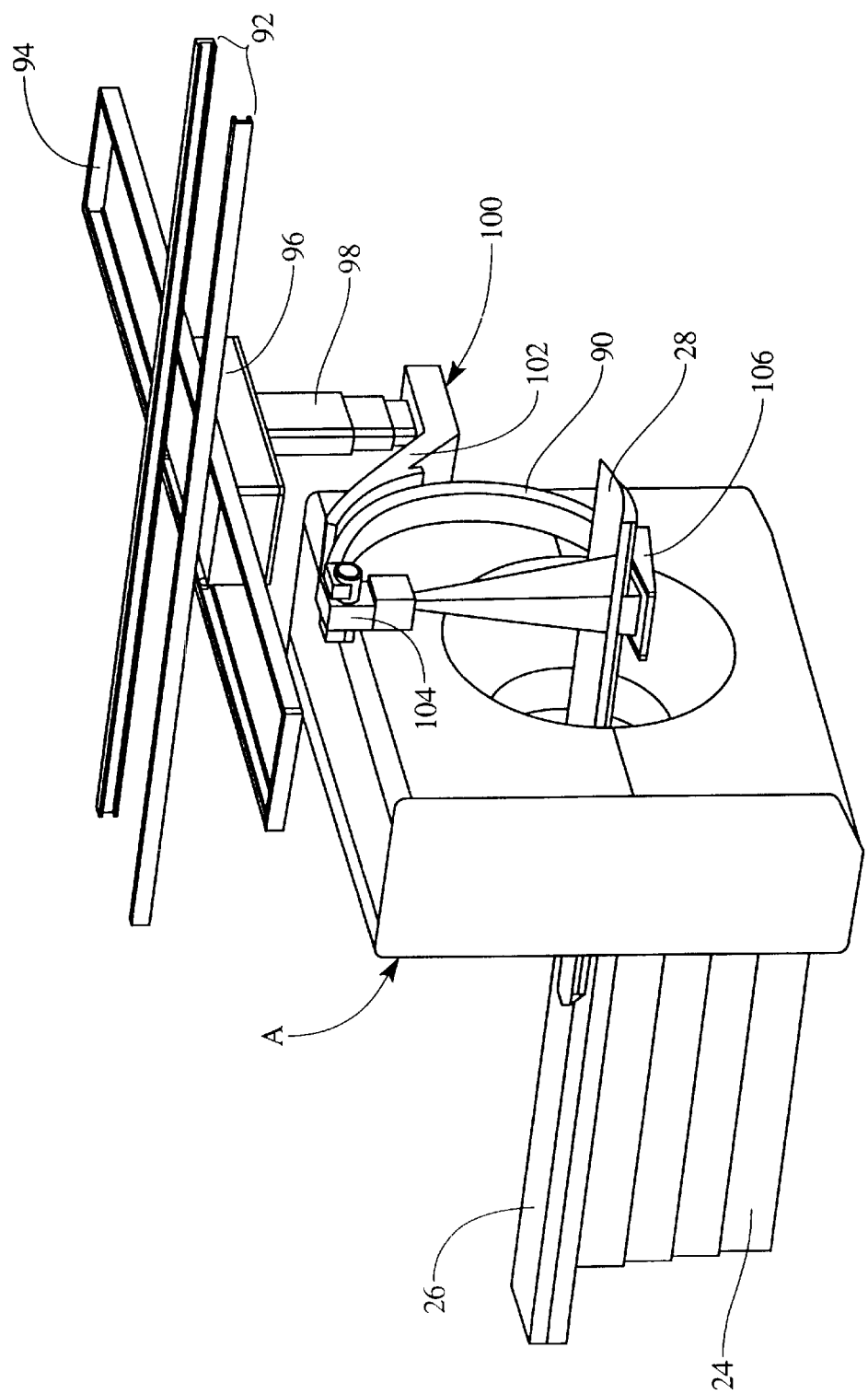
FIG. 9 is a perspective view of a CT scanner with the overhead C-arm of FIG. 7 positioned behind the CT gantry.

Referring now to FIGS. 7–9, the C-arm can be a stand-alone device which is mounted near the gantry and which provides the same functions described above. In particular, a C-arm 90 is suspended from a ceiling via a mounting structure such as an overhead track system G including first rails 92, and transverse rails 94 which are movable along the first rails 92. A trolley 96 is movably secured to the transverse rails 94 in directions transverse to the rails 92. A telescopic support arm 98 extends from the trolley 96. A cantilevered beam 100 extends from the telescopic arm 98 to support the C-arm 90. To reduce the torque applied to the beam 100, the C-arm is secured to an upwardly angled end portion 102 of the beam 100 which reduces the separation between the C-arm and the telescopic arm 98.

A fluoroscopic x-ray source or tube 104 is secured to an upper free end of the C-arm 90, and an opposing x-ray detector 106 is secured to the lower free end of the C-arm 90. As stated above, the x-ray source 104 can include a fixed or rotating anode x-ray tube with an integral or separate high voltage supply, and the detector 106 includes an amorphous silicon flat panel image receptor or array 108.

As shown in FIG. 8, the overhead track system G is oriented above the diagnostic scanner so that the C-arm 90 may be positioned in a stored position remote from the gantry, and positioned in an operating position between the patient table 24 and the front of the gantry A. In particular, the C-arm 90 may be positioned with the detector 106 substantially adjacent the patient rail 26 so that the patient couch 28 may be driven between the x-ray source 104 and the detector 106. Alternatively, as shown in FIG. 5, the C-arm 90 may be positioned in an operating position adjacent the rear of the gantry A so that the patient couch 28 must be driven through the bore of the gantry before passing between the x-ray source 104 and the detector 106.

Figure 10:
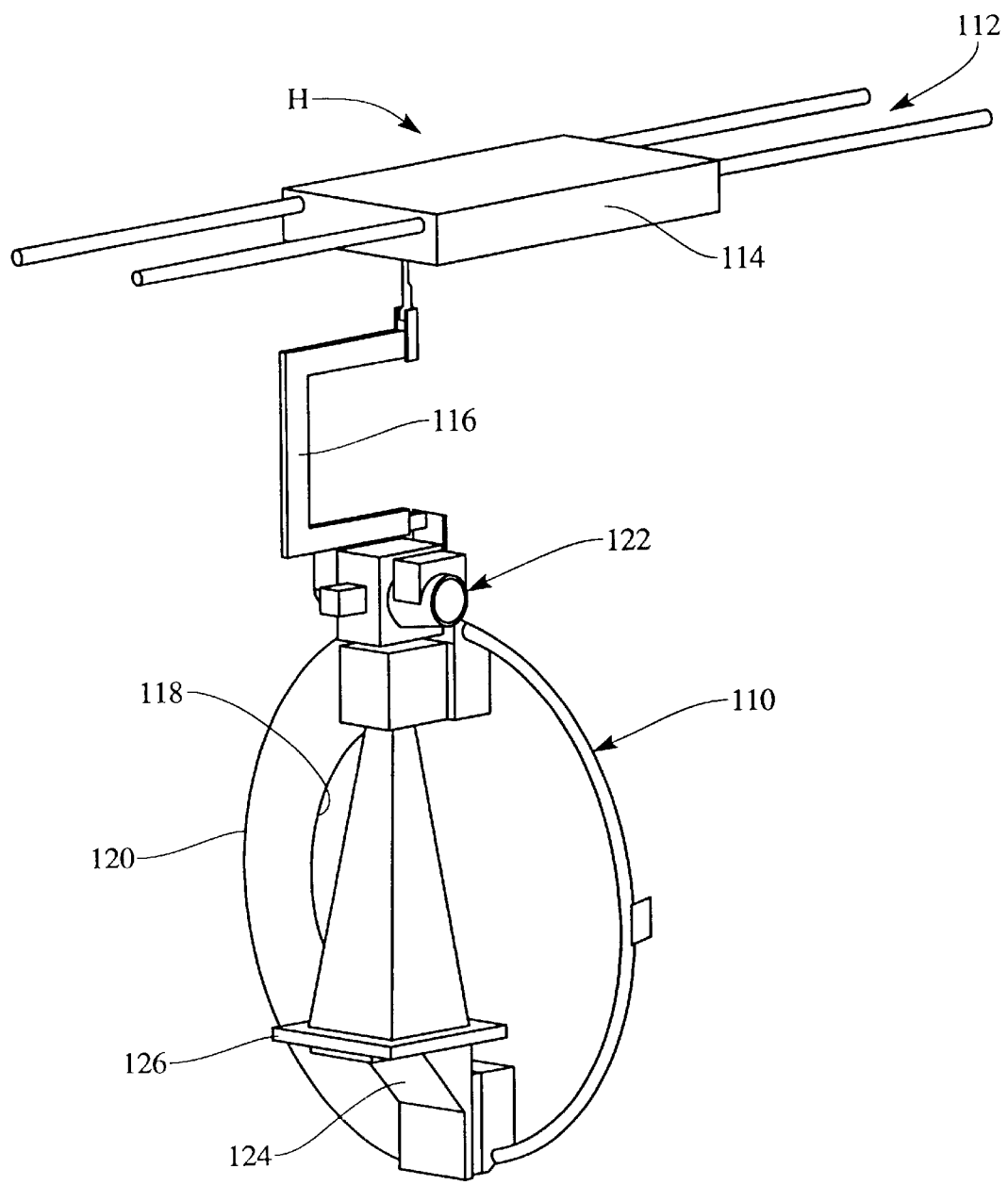
FIG. 10 is a perspective view of a third embodiment of an integrated fluoro-assist device having an annular support ring mounted to an overhead track.
Figure 11:
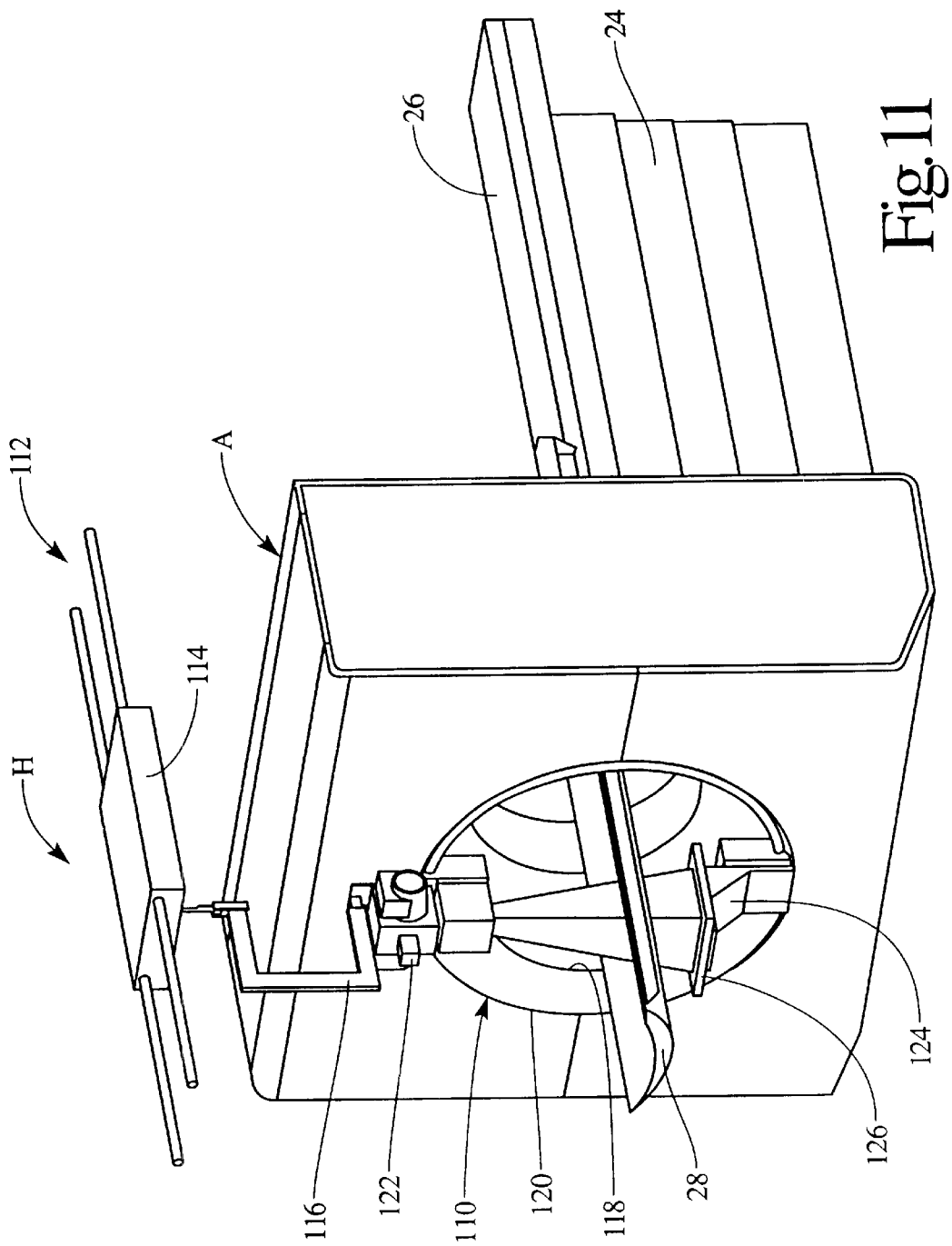
FIG. 11 is a perspective view of a CT scanner with the annular support ring of FIG. 10 positioned within the CT bore from behind the gantry.
Figure 12:
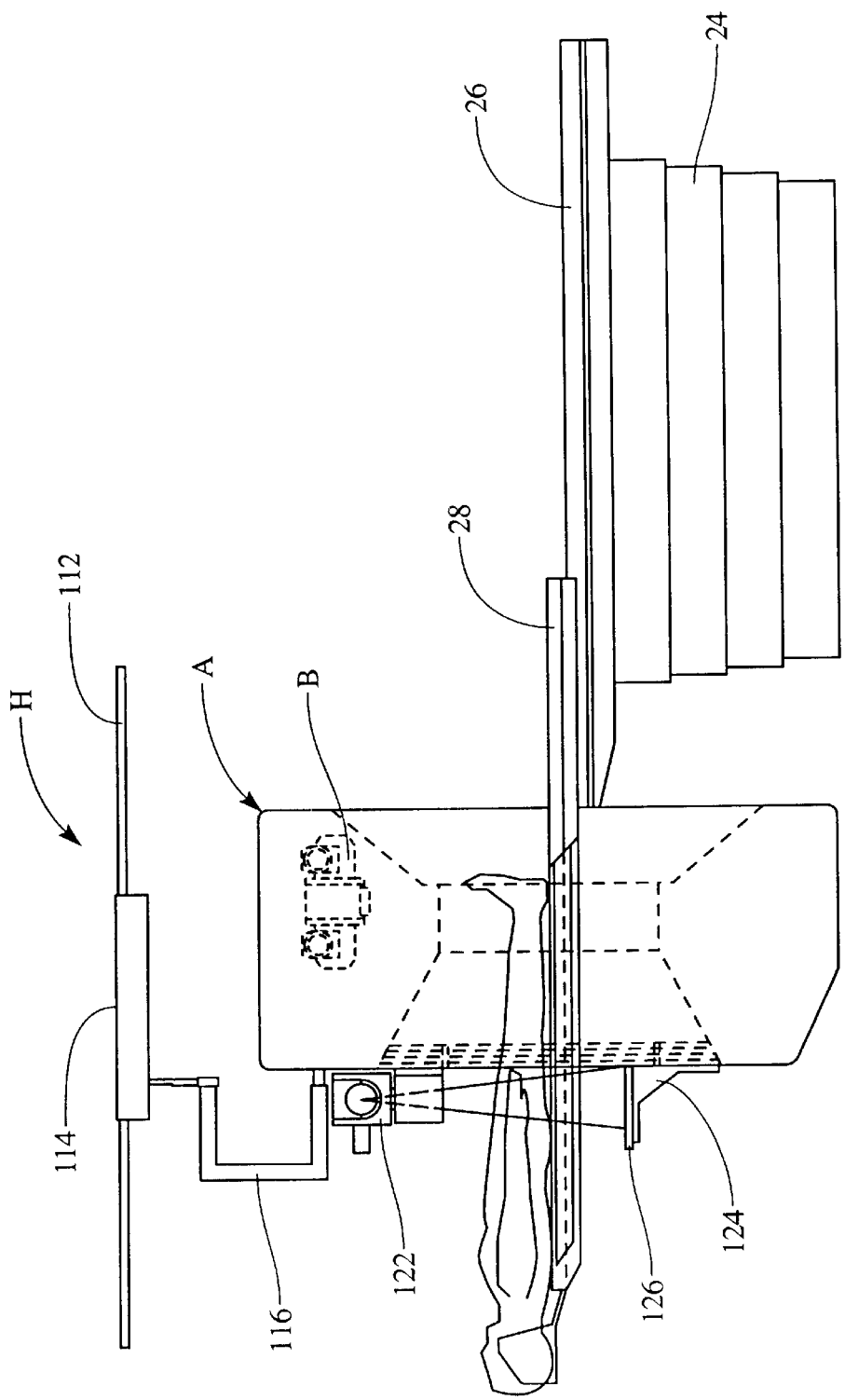
FIG. 12 is a side elevation view of the integrated CT-fluoro-assist scanner of FIG. 11.

Referring now to FIGS. 10–12, a support member such as a ring 110 is suspended from a mounting structure such as an overhead track system H which includes parallel rails 112 and a trolley 114 movably secured to the rails 112. A support arm 116 is suspended from the trolley 114. The support ring 110 is secured to a cantilevered lower portion of the support arm 116. The support ring 110 defines a tapered, annular side wall having a first diameter at an end edge 118, and a second diameter greater than the first diameter, at an opposing end edge 120.

A fluoroscopic x-ray source or tube 122 is secured to an upper portion of the support ring 110 adjacent the end edge 120. An angled support 124 is secured to a lower portion of the support ring 110 adjacent the end edge 120. An amorphous silicon flat panel detector 126 is secured to a planar surface of the support 124 substantially beneath the x-ray source 122.

The overhead track system H is oriented above the diagnostic scanner so that the support ring 110 can be positioned in a stored position remote from the gantry and in an operating position at least partially within the bore of the gantry A. In particular, the tapered annular sidewall defining the support ring 110 conforms to the mutually tapered sidewall defining the bore of the gantry to facilitate accurately and repeatably positioning the x-ray source 122 and the detector 126 relative to the patient couch 28 which is driven through the bore. Thus, with the support ring positioned in the bore, the patient couch 28 may be driven through the gantry and between the x-ray source 122 and the detector 126 which are positioned immediately adjacent the rear of the gantry.

Figure 13:
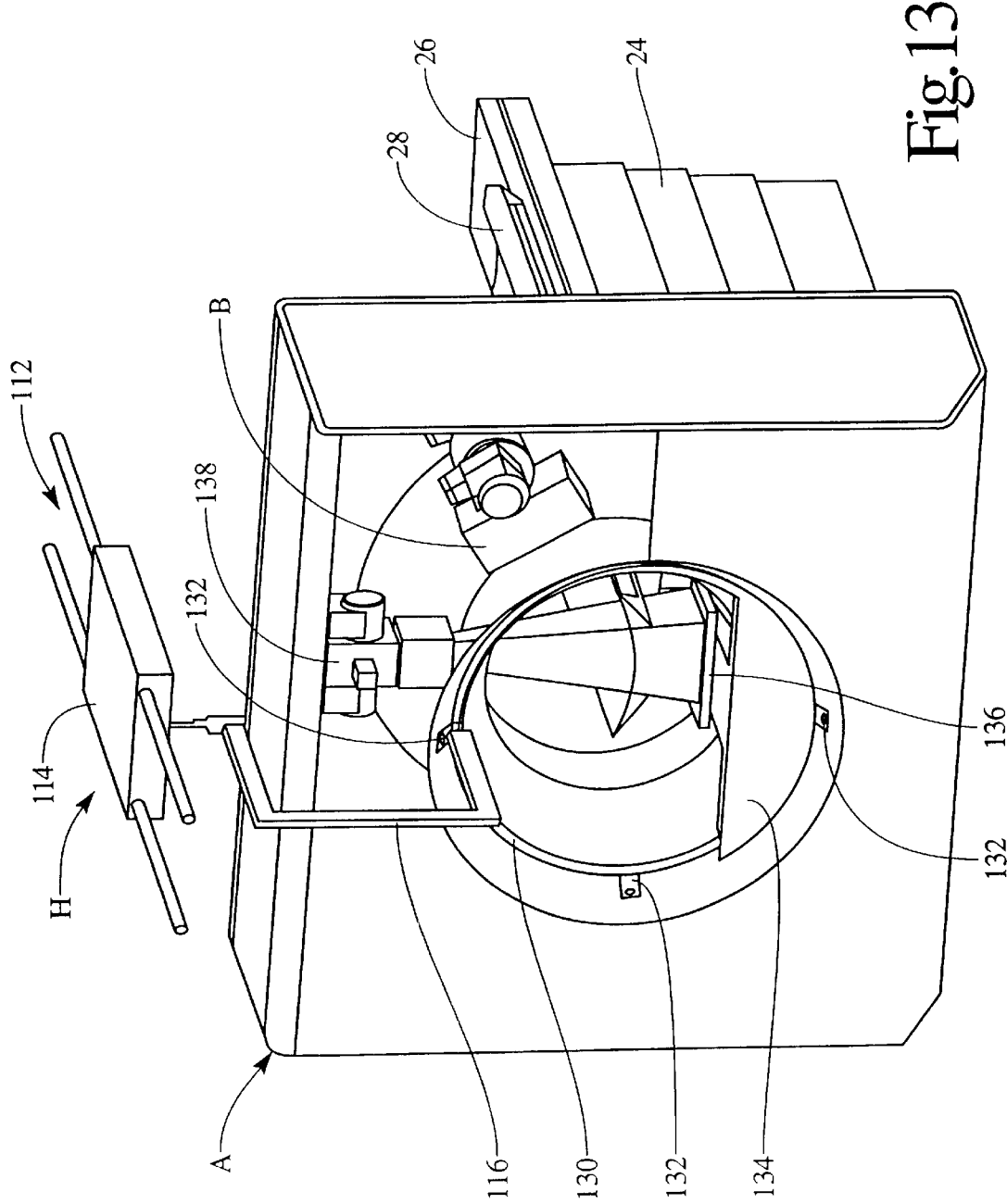
FIG. 13 is a perspective view of a CT scanner having separate fluoroscopic and CT x-ray sources mounted within the gantry and incorporating an integrated fluoro-assist device having an annular ring mounted to an overhead track for supporting a flat panel fluoroscopic detector within a bore of the CT scanner.
Figure 14:
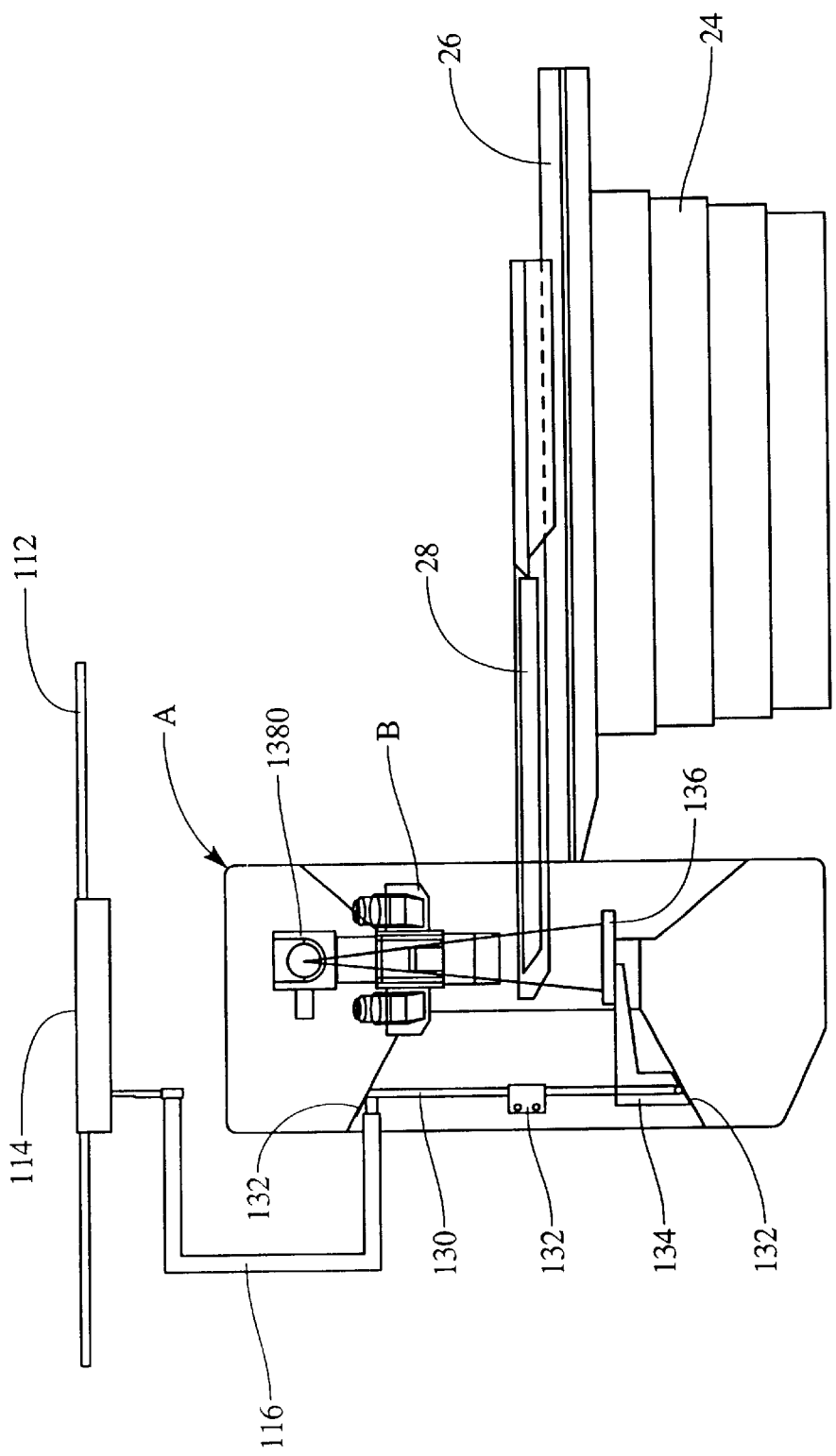
FIG. 14 is a side elevation view of the integrated CT-fluoro-assist scanner of FIG. 13.

Referring now to FIGS. 13 and 14, an alternate support ring 130 is suspended from the previously described overhead track system H for movement between a stored position remote from the gantry and an operating position. The support ring 130 is secured to the cantilevered lower portion of the support arm 116 which is suspended from the trolley 114. The support ring 130 has a diameter which substantially conforms to a diameter of an intermediate portion of a tapered sidewall defining the cylinder 10 within the gantry A. A plurality of tabs 132 extend radially from the support ring 130. The tabs also extend at an angle from a plane of the support ring, which angle substantially defines the taper of the cylinder sidewall proximate the support ring, when positioned within the cylinder 10. The tabs 132 facilitate accurately and repeatably positioning the support ring at a desired operating position within the cylinder 10.

A platform 134 is secured to a lower portion of the support ring 130 and extends transverse to the support ring 130. An amorphous silicon flat panel detector 136 is secured to an upper surface of the platform 134. A fluoroscopic x-ray source or tube 138 is mounted to the rotating gantry portion C, and is angularly offset from the x-ray source B. The overhead track system G is oriented above the diagnostic scanner so that the support ring 130 can be positioned within the cylinder 10 from the rear of the gantry A so that the detector 136 is positioned substantially beneath the x-ray source 138 within the patient examination region 12. When the support ring is fully positioned within the cylinder 10, the tabs 132 contact the tapered sidewall defining the cylinder 10 to accurately and repeatably position the detector 136 relative to the x-ray source 138 and patient couch 28.

Figure 15:
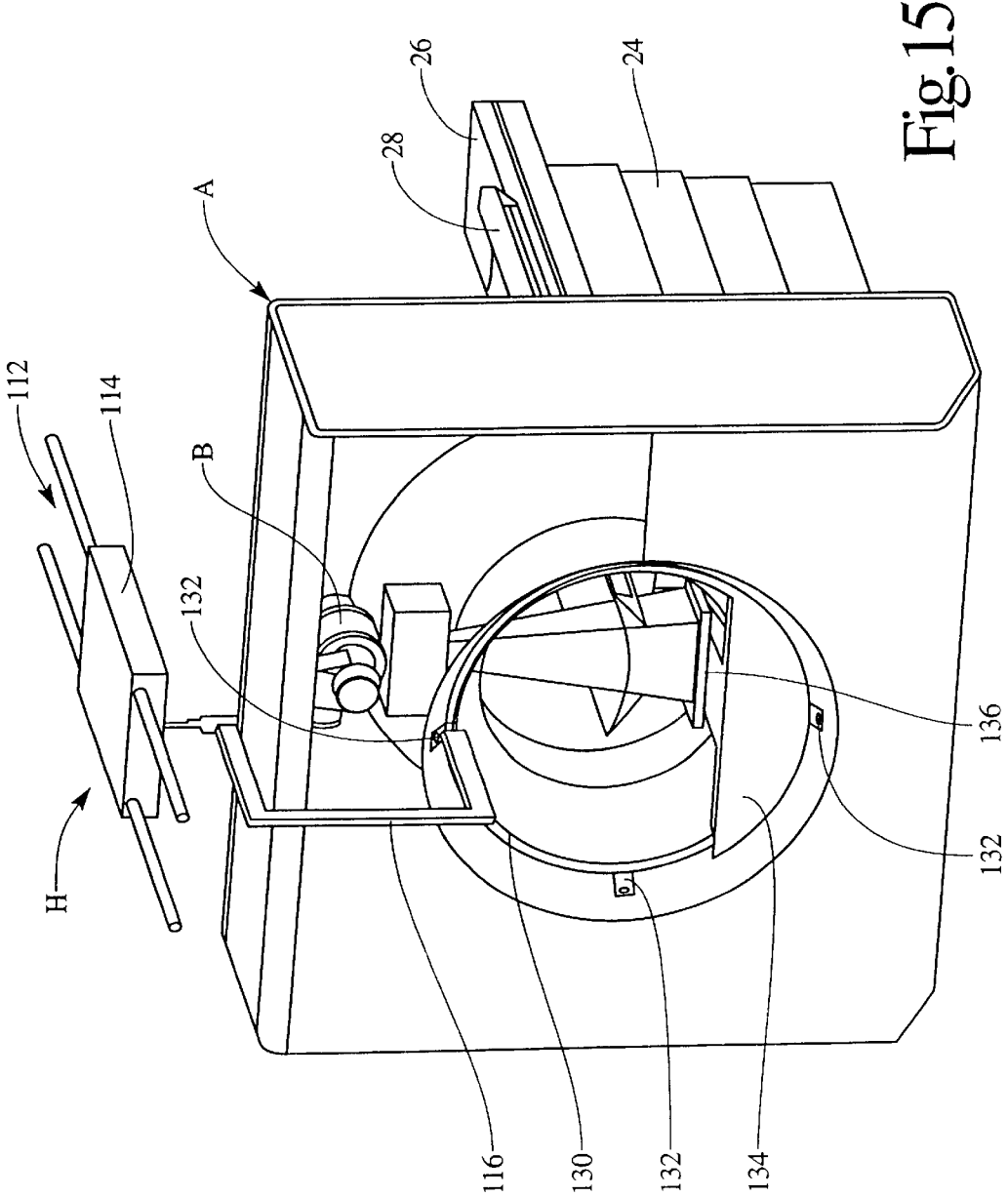
FIG. 15 is a perspective view of a CT scanner having an integrated fluoroscopic/CT x-ray source mounted within the gantry and incorporating an integrated fluoro-assist device having an annular ring mounted to an overhead track for supporting a flat panel fluoroscopic detector within the bore of a CT scanner.
Figure 16:
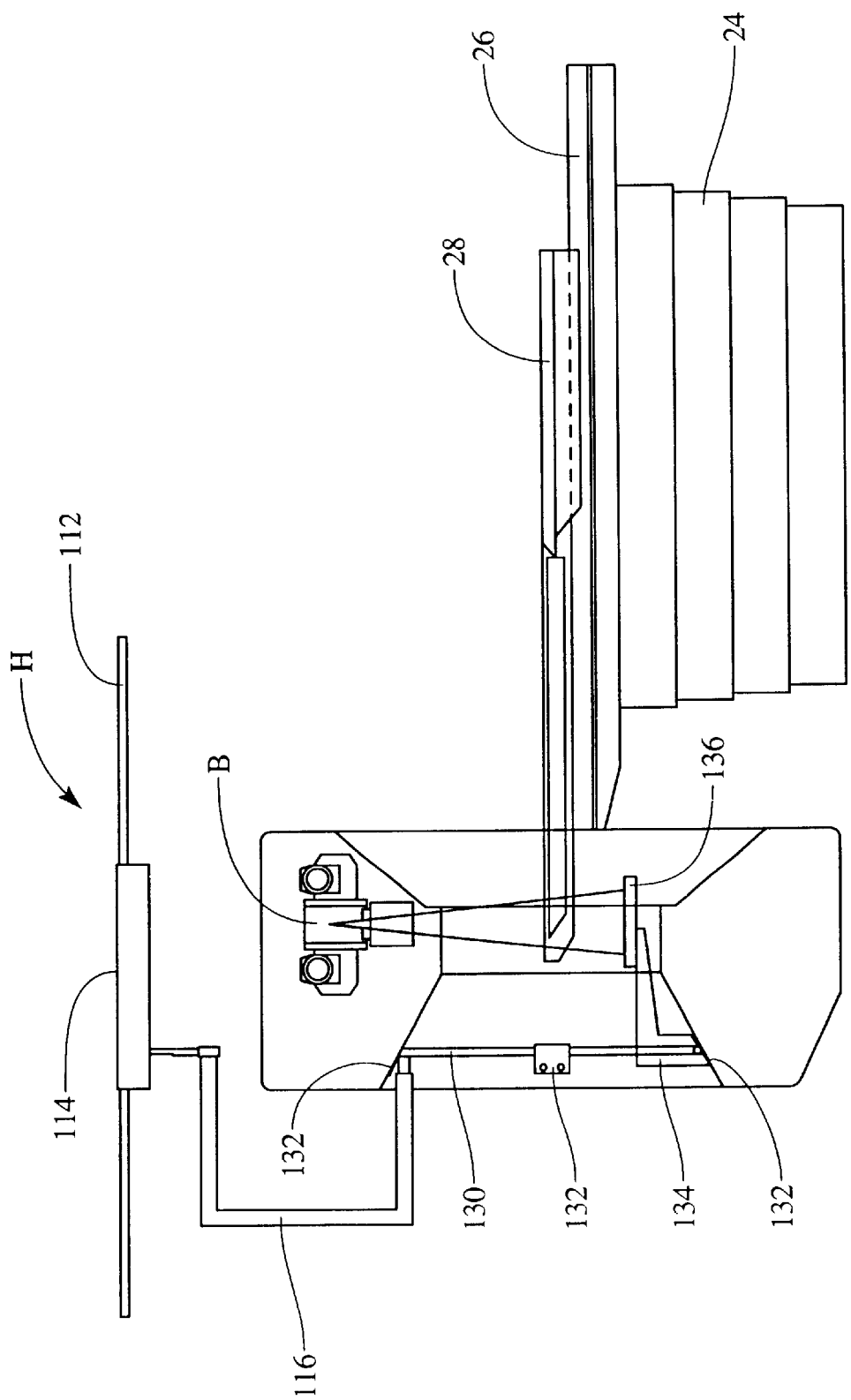
FIG. 16 is a side elevation view of the integrated CT-fluoro-assist scanner of FIG. 15.

The diagnostic scanner incorporates an indexing means for driving or rotating the low power x-ray source 138 to a predetermined position (e.g. a twelve o'clock position) substantially opposite to that of the detector 136 prior to initiating a fluoroscopic imaging procedure. It should be appreciated that the x-ray source 138 may also be mounted to the non-rotating gantry portion A in a position either radially or axially offset from the x-ray source B mounted on the rotating gantry portion C. Alternatively, as shown in FIGS. 15 and 16, the support ring 130 may be used in conjunction with the x-ray source B mounted in the rotating gantry portion C. The x-ray source is operated in a reduced power, fluoroscopic mode when positioned opposite to the fluoroscopic detector 136.

Figure 17:
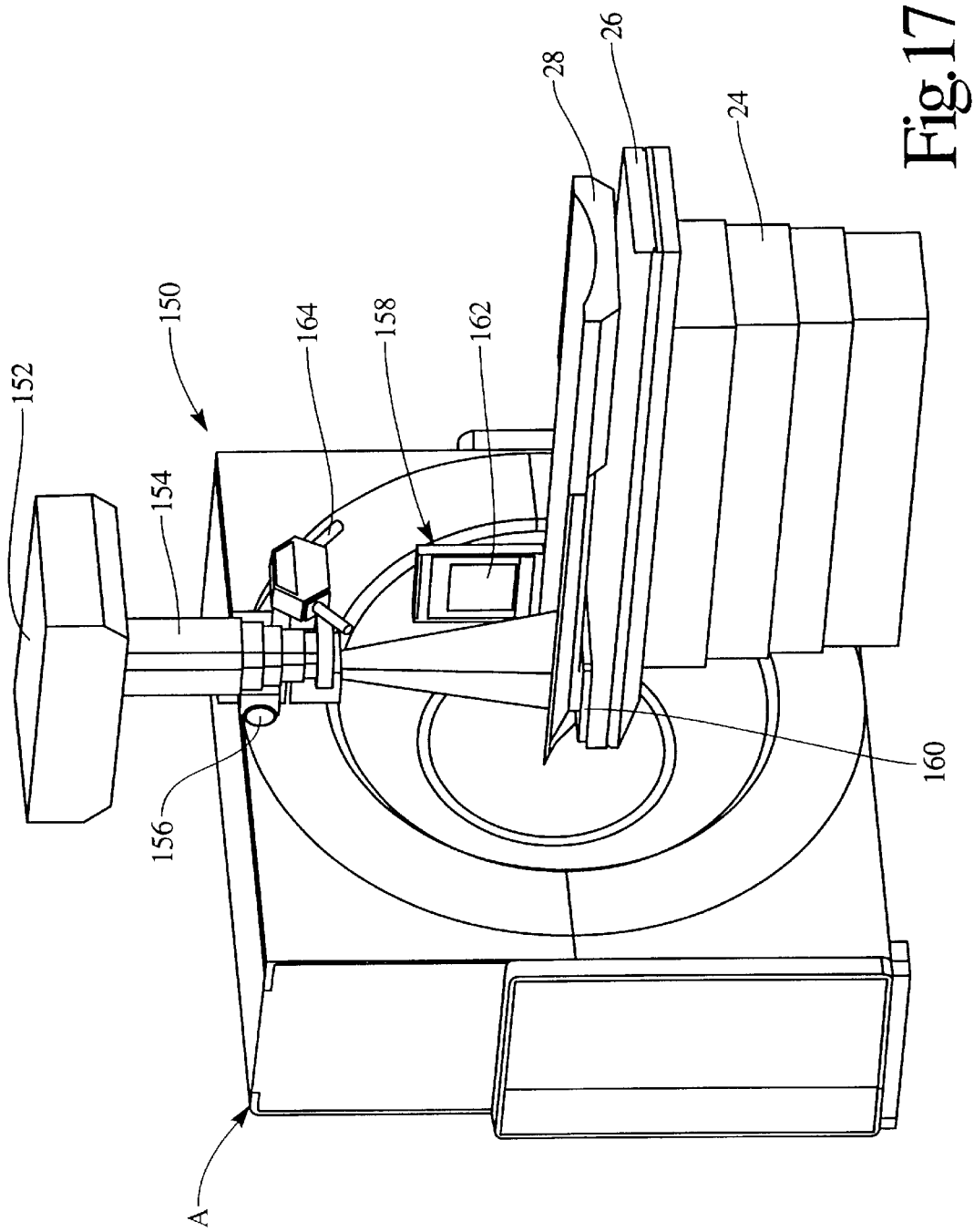
FIG. 17 is a perspective view of a CT scanner incorporating a sixth embodiment of an integrated fluoro-assist device with a track-mounted support arm positioned for fluoroscopic imaging in a coronal plane.
Figure 18:
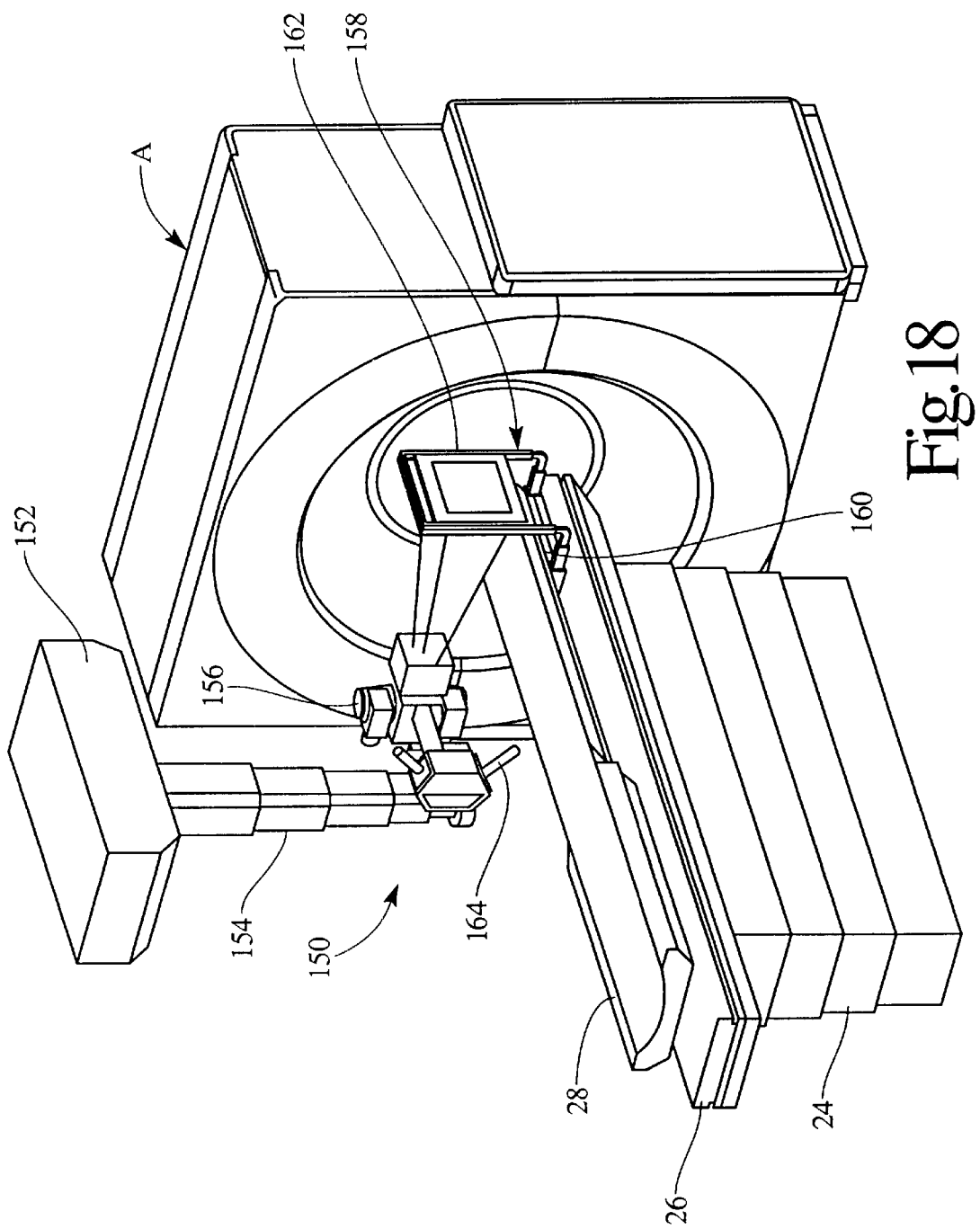
FIG. 18 is a perspective view of the CT scanner of FIG. 17 with the track-mounted support arm positioned for fluoroscopic imaging in a sagittal plane.

Referring now to FIGS. 17 and 18, a fluoro-assist device 150 for a diagnostic scanner includes an overhead track system, for example the track system as shown in FIGS. 3–11, which supports a movable trolley 152. A telescopic support arm 154 extends from the trolley 152. A lowermost free end of the support arm has a fluoroscopic x-ray source or tube assembly 156 pivotally secured thereto. An L-shaped image detector frame 158 includes a first amorphous silicon flat panel detector 160 mounted to a first leg of the frame, and includes a second amorphous silicon flat panel detector 162 mounted to a second leg of the frame. The first detector 160 extends substantially transverse to the second detector 162.

The first detector 160 is oriented horizontally between the patient beam 26 and the patient couch 28, while the second detector 162 extends substantially upright from the patient beam 26 adjacent the patient couch 28. When fluoroscopic imaging in a coronal plane is desired, the trolley 152 and support arm 154 are adjusted to position the x-ray source assembly 156 substantially above the first detector 160, as shown in FIG. 17. Likewise, when fluoroscopic imaging in a sagittal plane is desired, the trolley 152 and support arm 154 are adjusted to position the x-ray source assembly 156 laterally across from the second detector 162, as shown in FIG. 18. Operator graspable handles 164 assist in the accurate positioning and aiming of the x-ray source.

Figure 19:
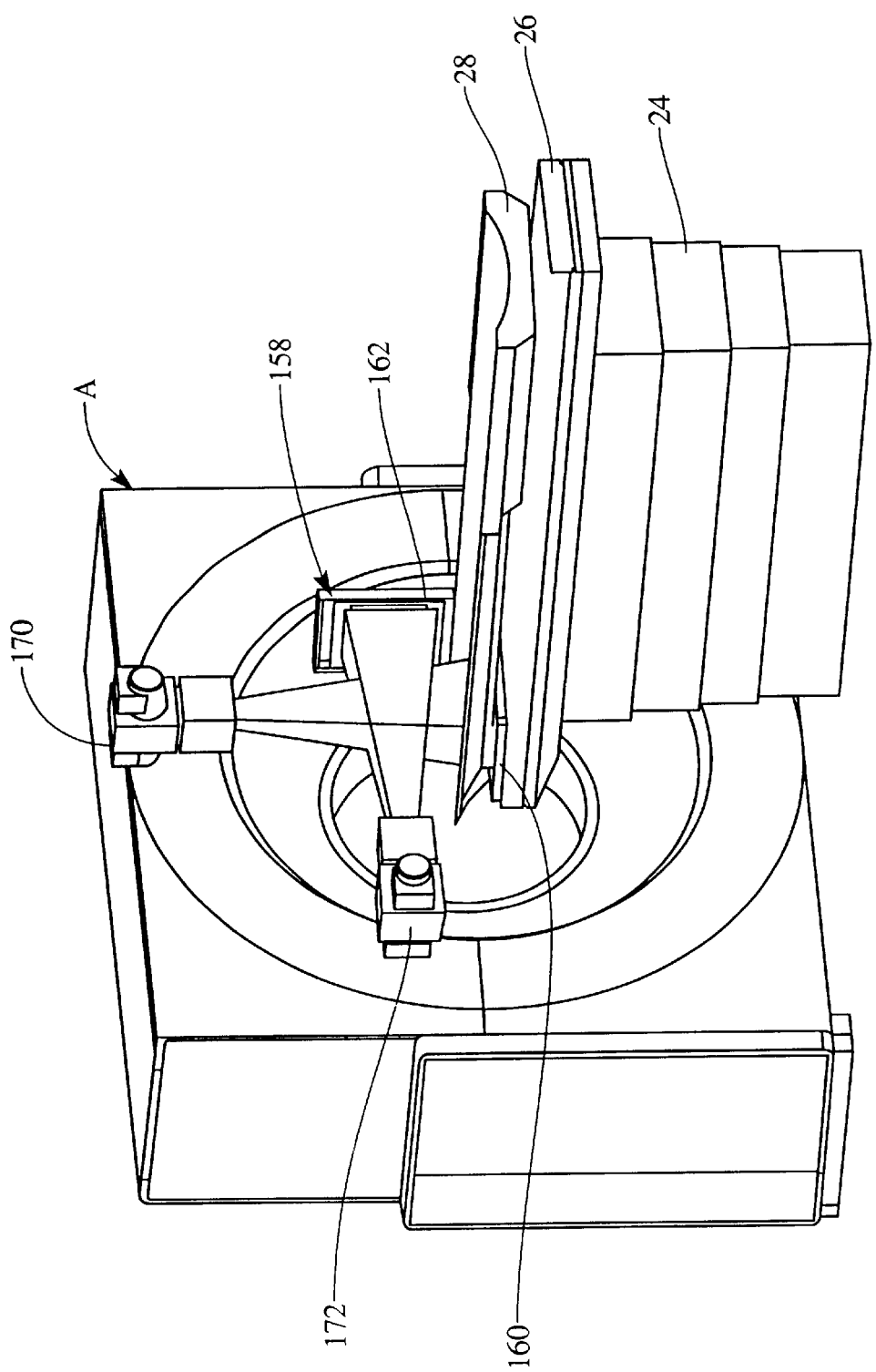
FIG. 19 is a perspective view of a CT scanner incorporating a seventh embodiment of an integrated fluoro-assist device.

The image detector frame 158 can also be used in conjunction with two discrete fluoroscopic x-ray sources, as shown in FIG. 19. In particular, a first x-ray source 170 is fixedly mounted to the front of the gantry A substantially above the first detector 160. Likewise, a second x-ray source 172 is mounted, movably or fixedly, to the front of the gantry A substantially lateral from the second detector 162. In one mode, the x-ray sources 170, 172 are used separately to generate fluoroscopic images in each of the coronal or sagittal planes. In another mode, the x-ray sources 170, 172 are used together to generate volumetric or 3D fluoroscopic images in a known manner.

Figure 20:
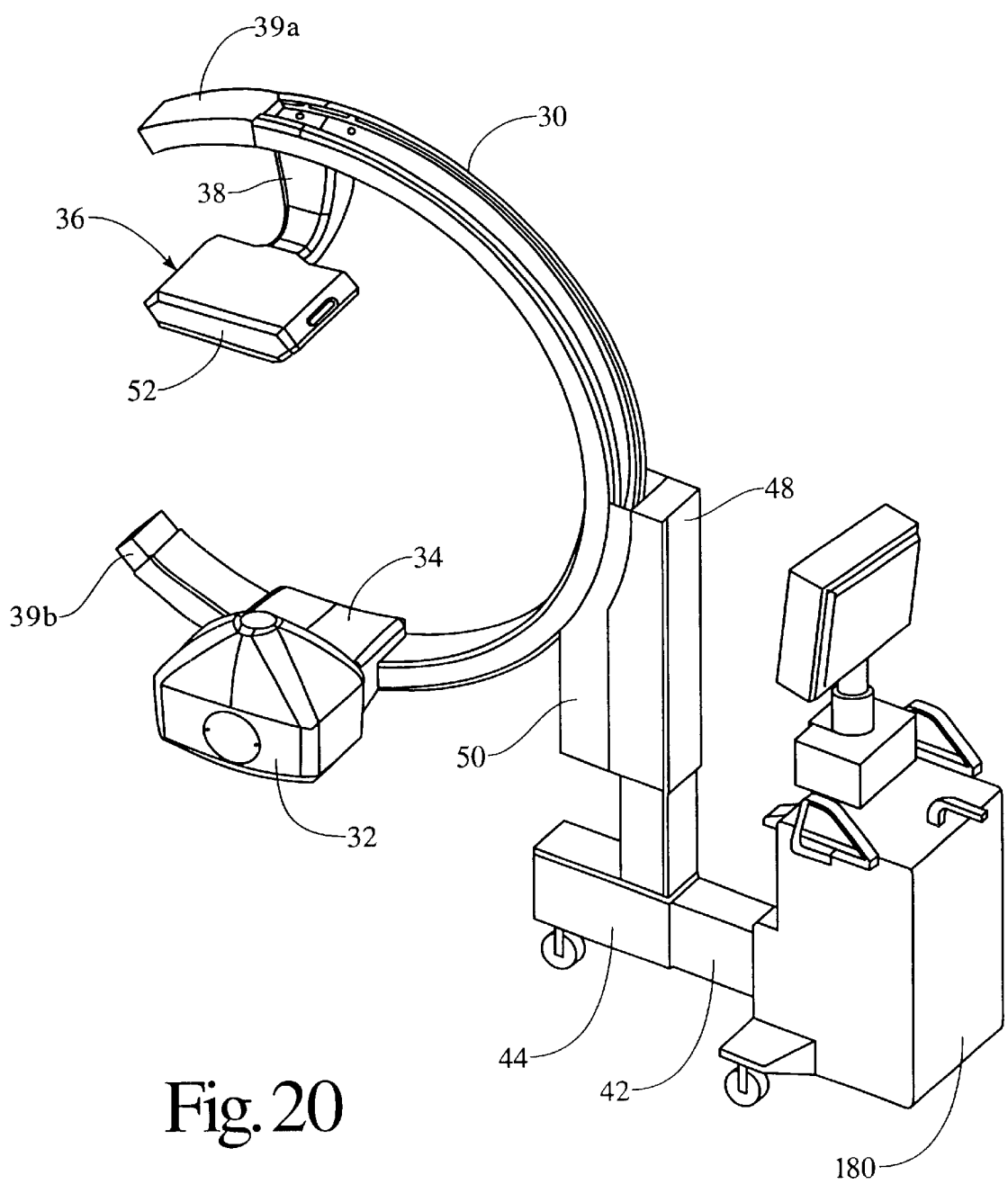
FIG. 20 is a perspective view of an eighth embodiment of a fluoro-assist device.

Referring to FIG. 20, the fluoroscopy or fluoro-assist device D, as described above with reference to FIGS. 1–6, can also be mounted to a mobile cart 180. In addition, with reference to FIG. 21, the fluoroscopy or fluoro-assist device D can be mounted to an MRI device 200. The MRI device includes a frame 202 housing a main magnet 204 for generating a temporally constant main magnetic field through an examination region 206. A series of gradient coils 208 in conjunction with gradient amplifiers (not shown) generate gradient magnetic fields across the examination region. The gradient amplifiers generate current pulses which result in corresponding gradient magnetic field pulses along the x-, y-, and z-axis for phase encoding, and read out or frequency encoding. A radio frequency coil 210 and a radio frequency transmitter (not shown) generate RF excitation pulses for exciting magnetic resonance and inversion or other pulses for manipulating the magnetic resonance.

Figure 21:
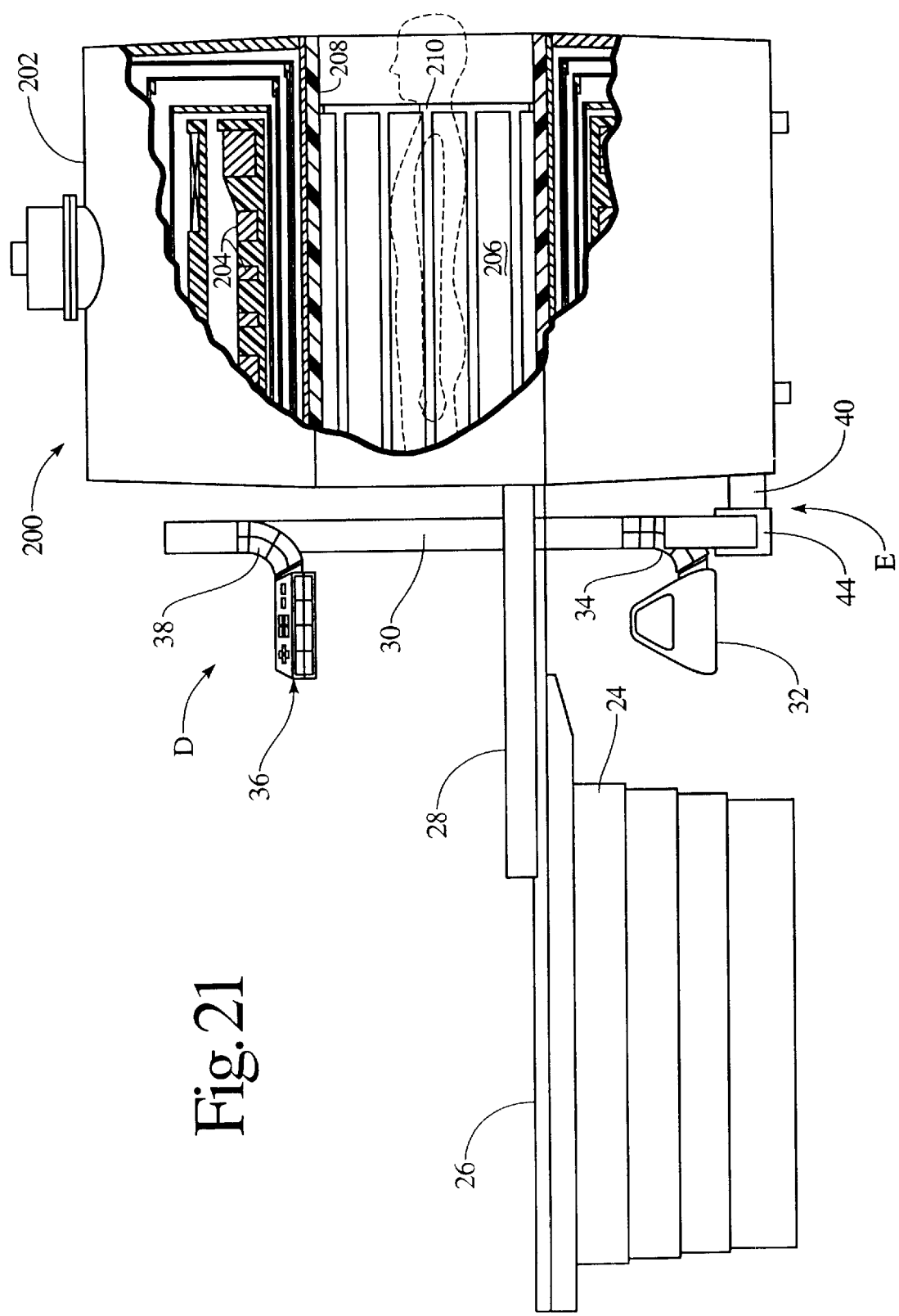
FIG. 21 is a side elevation view of the Magnetic Resonance Imaging (MRI) apparatus of FIG. 1 with the C-arm shown in the operating position.

The patient table 24 is positioned adjacent the MRI device so as to extend from the examination region 206 in a first direction substantially along a central axis of a bore defining the examination region 206. The fluoroscopy device D is secured to the frame 200 by the mounting structure E for movement between an operating position as shown in FIG. 21, and a stored position. Alternatively, the fluoroscopy device can be suspended from the overhead track system G or H as described above.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

For instance, although the fluoro-assist device of the present invention was described as providing fluoroscopic images, the fluoro-assist device could, with increased power of the x-ray source, provide radiographic exposures in addition to fluoroscopic exposures.

Further, the fluoro-assist device D, which incorporates an amorphous silicon flat panel image receptor, may also be mechanically coupled to other medical diagnostic imaging systems such as a nuclear medicine scanner, etc. in the same manner as described above. Thus, the fluoro-assist device of the present invention can at least provide pilot scans for other diagnostic imaging procedures.

Having thus described the preferred embodiments, the invention is now claimed to be:

1. A fluoroscopy imaging device which generates at least one of a fluoroscopic image representation and a radiographic image representation of an object, the fluoroscopy imaging device including:
   a mobile cart;
   a fluoroscopic x-ray source for transmitting x-rays;
   a flat panel image receptor for detecting the x-rays and generating signals indicative of the detected x-rays, the flat panel image receptor being mounted in a housing having a first control panel proximate one end thereof and a second control panel proximate a second end thereof; and
   a support member secured to the mobile cart for supporting the fluoroscopic x-ray source and the flat panel image receptor.

2. A diagnostic imaging device comprising:
   a base;
   a support member;
   an x-ray source secured to a first portion of the support member, the x-ray source generating x-rays;
   a flat panel image receptor secured to a second portion of the support member remote from the x-ray source, the image receptor detecting x-rays and generating signals indicative of detected x-rays, the signals being used to generate one of fluoroscopic image representations and radiographic image representations of an object positioned between the x-ray source and the image receptor, the flat panel image receptor being mounted in a housing having a first control panel proximate one end thereof and a second control panel proximate a second end thereof;
   a mounting structure that couples the support member to the base such that the support member is movable relative to the base; and
   means for repositioning the base to located the object substantially between the x-ray source and the image receptor.

3. The diagnostic imaging device of claim 2, wherein the flat panel image receptor includes a scintillating layer which coverts x-rays into light, and an amorphous silicon glass substrate supporting a plurality of photodiodes which convert light generated by the scintillating layer into signals.

4. The diagnostic imaging device of claim 2, wherein the flat panel image receptor is offset from a plane of the support member by a first cantilevered arm, and the x-ray source is offset from the plane of the support member by a second cantilevered arm.

5. The diagnostic imaging device of claim 2, wherein the support member includes a C-arm.

6. The diagnostic imaging device of claim 2, wherein the mounting structure includes means for rotating the support member through an arc of at least 180° relative to the mounting structure.

7. The diagnostic imaging device of claim 2, wherein a centerline extending between the x-ray source and the flat panel image receptor intersects an orbital axis of the support member.

8. The diagnostic imaging device of claim 2, wherein the mounting structure includes:
   a lateral support member having a longitudinal track associated therewith;
   a first upright support member movably secured to the lateral support member for substantial horizontal movement along the track;
   a second upright support member movably secured to the first upright support member for substantial vertical movement along a common longitudinal axis of the first and second upright support members, the support arm being rotatably supported by the second upright support member.

9. The diagnostic imaging device of claim 2, wherein:
   the support arm includes a C-arm having an open channel extending longitudinally along an exterior surface of the C-arm; and
   the mounting structure includes a hose guide for guiding a control cable at least partially into the open channel when the C-arm is orbited in a first direction and for guiding the control cable into a service loop from the open channel when the C-arm is orbited in a second direction.

10. The diagnostic imaging device of claim 2, further including a display monitor mounted to the base for displaying the one of fluoroscopic image representations and radiographic image representations.

11. The diagnostic imaging device of claim 2, wherein the means for repositioning including a plurality of wheels mounted to the base.

12. A diagnostic imaging device comprising:
   a base;
   a support member, the support member including a C-arm having an open channel extending longitudinally along an exterior surface of the C-arm;
   an x-ray source secured to a first portion of the support member, the x-ray source generating x-rays;
   a flat panel image receptor secured to a second portion of the support member remote from the x-ray source, the image receptor detecting x-rays and generating signals indicative of detected x-rays, the signals being used to generate one of fluoroscopic image representations and radiographic image representations of an object positioned between the x-ray source and the image receptor;
   a control cable coupled to at least one of the x-ray source and the flat panel image receptor, and a cable control mechanism that regulates the tension of the control cable during rotation of the support member;

a mounting structure that couples the support member to the base such that the support member is movable relative to the base, the mounting structure including a hose guide for guiding the control cable at least partially into the C-arm open channel when the C-arm is orbited in a first direction and for guiding the control cable into a service loop from the open channel when the C-arm is orbited in a second direction; and means for repositioning the base to located the object substantially between the x-ray source and the image receptor.

13. A method of performing an interventional medical procedure using a fluoroscopy device and a separate one of a computed tomographic device and a magnetic resonance imaging device, the fluoroscopy device including a base, a support member, a fluoroscopic x-ray source secured to a first portion of the support member, a flat panel image receptor secured to a second portion of the support member remote from the x-ray source, a mounting structure that couples the support member to the base such that the support member is movable relative to the base, and means for repositioning the base, the method comprising:

positioning an object on a support associated with the one of the computed tomographic device and the magnetic resonance imaging device;

actuating one of the computed tomographic device and the magnetic resonance imaging device to generate a high resolution image of the object;

positioning the fluoroscopy device base to locate the object substantially between the x-ray source and the image receptor;

actuating the x-ray source and flat panel image receptor to generate signals for reconstructing fluoroscopic image representations the object positioned between the x-ray source and the image receptor, the step actuating the x-ray source and flat panel image receptor including:

operating a first control panel adjacent a first side of the flat panel image receptor when the flat panel image receptor is in a first orientation, and operating a second control panel adjacent a second side of the flat panel image receptor when the flat panel image receptor is in a second orientation rotationally spaced from the first orientation; and performing the interventional procedure in accordance with the high resolution image and the fluoroscopic images.

14. The method of claim 13, wherein:

the fluoroscopy device includes a housing for the flat panel image receptor, the housing including a first control panel proximate one end of the housing and a second control panel proximate a second end of the housing; and the step of actuating the x-ray source and flat panel image receptor includes the step of utilizing at least one of the first control panel and the second control panel to control the fluoroscopy device.

15. The method of claim 13, further including:

moving the fluoroscopy device support arm relative to the fluoroscopy device base to locate the object substantially between the x-ray source and the image receptor.

16. The method of claim 13, wherein the step of positioning the base includes:

rotating the fluoroscopy device support member around a longitudinal axis of the object.

17. The method of claim 13, wherein:

the fluoroscopy device mounting structure includes a lateral support member having a longitudinal track associated therewith, a first upright support member movably secured to the lateral support member for substantial horizontal movement along the track, a second upright support member movably secured to the first upright support member for substantial vertical movement along a common longitudinal axis of the first and second upright support members; and wherein the step of positioning the base includes extending the fluoroscopy device support member laterally relative to the fluoroscopy device base.

18. The method of claim 13, wherein:

the fluoroscopy device mounting structure includes a lateral support member having a longitudinal track associated therewith, a first upright support member movably secured to the lateral support member for substantial horizontal movement along the track, a second upright support member movably secured to the first upright support member for substantial vertical movement along a common longitudinal axis of the first and second upright support members; and the step of positioning the base includes extending the fluoroscopy device support member vertically relative to the fluoroscopy device base.

19. The method of claim 13, wherein:

the fluoroscopy device includes a display monitor mounted to the base; and the method further includes the step of displaying the one of fluoroscopic image representations and radiographic image representations on the display monitor.

20. The method of claim 13, wherein:

the means for repositioning the fluoroscopy device includes a plurality of wheels mounted to the base; and the step of positioning the fluoroscopy device base including rolling the base to locate the object substantially between the x-ray source and the image receptor.

* * * * *